US010369368B2

(12) United States Patent
Ryu et al.

(10) Patent No.: US 10,369,368 B2
(45) Date of Patent: *Aug. 6, 2019

(54) OPTIMAL PACING CONFIGURATION VIA VENTRICULAR CONDUCTION DELAYS

(71) Applicants: Kyungmoo Ryu, Palmdale, CA (US); Xiaoyi Min, Thousand Oaks, CA (US)

(72) Inventors: Kyungmoo Ryu, Palmdale, CA (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 315 days.

This patent is subject to a terminal disclaimer.

(21) Appl. No.: 15/172,993

(22) Filed: Jun. 3, 2016

(65) Prior Publication Data
US 2016/0279419 A1 Sep. 29, 2016

Related U.S. Application Data

(62) Division of application No. 12/632,519, filed on Dec. 7, 2009, now Pat. No. 9,381,363.

(51) Int. Cl.
*A61N 1/05* (2006.01)
*A61N 1/37* (2006.01)
(Continued)

(52) U.S. Cl.
CPC ........... *A61N 1/3684* (2013.01); *A61N 1/056* (2013.01); *A61N 1/368* (2013.01); *A61N 1/3686* (2013.01); *A61N 1/36514* (2013.01); *A61N 1/371* (2013.01); *A61N 1/3627* (2013.01); *A61N 1/37247* (2013.01)

(58) Field of Classification Search
CPC .... A61N 1/3627; A61N 1/368; A61N 1/3684; A61N 1/3686; A61N 1/371; A61N 1/37247
See application file for complete search history.

(56) References Cited

U.S. PATENT DOCUMENTS 4,940,052 A * 7/1990 Mann ................. A61N 1/36542
607/17
6,606,516 B2 * 8/2003 Levine ................. A61N 1/3627
607/9
(Continued)

*Primary Examiner* — Christopher A Flory

(57) ABSTRACT

An exemplary method for optimizing pacing configuration includes providing distances between electrodes of a series of three or more ventricular electrodes associated with a ventricle; selecting a ventricular electrode from the series; delivering energy to the ventricle via the selected ventricular electrode, the energy sufficient to cause an evoked response; acquiring signals of cardiac electrical activity associated with the evoked response via non-selected ventricular electrodes of the series; based on signals of cardiac electrical activity acquired via the non-selected ventricular electrodes and the distances, determining conduction velocities; based on the conduction velocities, deciding if the selected ventricular electrode is an optimal electrode for delivery of a cardiac pacing therapy; and, if the selected ventricular electrode comprises an optimal electrode for delivery of the cardiac pacing therapy, calling for delivery of the cardiac pacing therapy using the selected ventricular electrode. Various other methods, devices, systems, etc., are also disclosed.

7 Claims, 13 Drawing Sheets

(51) Int. Cl.
*A61N 1/362* (2006.01)
*A61N 1/365* (2006.01)
*A61N 1/368* (2006.01)
*A61N 1/372* (2006.01)

(56) References Cited

U.S. PATENT DOCUMENTS

| | | | | |
|---|---|---|---|---|
| 6,643,546 B2* | 11/2003 | Mathis | A61N 1/3627 | 607/123 |
| 7,013,176 B2* | 3/2006 | Ding | A61N 1/3627 | 607/9 |
| 7,239,913 B2* | 7/2007 | Ding | A61N 1/368 | 607/27 |
| 7,440,804 B1* | 10/2008 | Min | A61N 1/3622 | 607/28 |
| 7,637,867 B2* | 12/2009 | Zdeblick | A61B 5/0422 | 600/300 |
| 7,787,951 B1* | 8/2010 | Min | A61B 5/04012 | 607/17 |
| 7,917,214 B1* | 3/2011 | Gill | A61N 1/372 | 607/27 |
| 7,941,217 B1* | 5/2011 | Pei | A61N 1/365 | 607/11 |
| 7,941,219 B2* | 5/2011 | Sathaye | A61N 1/371 | 607/28 |
| 8,010,194 B2* | 8/2011 | Muller | A61B 5/0452 | 607/14 |
| 8,036,743 B2* | 10/2011 | Savage | A61N 1/36185 | 607/5 |
| 8,160,700 B1* | 4/2012 | Ryu | A61N 1/3627 | 607/25 |
| 8,175,707 B1* | 5/2012 | Wright | A61N 1/3627 | 607/18 |
| 9,381,363 B2* | 7/2016 | Ryu | A61N 1/368 | |
| 2003/0023130 A1* | 1/2003 | Ciaccio | A61B 5/04011 | 600/12 |
| 2004/0049235 A1* | 3/2004 | Deno | A61N 1/36114 | 607/9 |
| 2004/0106958 A1* | 6/2004 | Mathis | A61N 1/3627 | 607/11 |
| 2004/0147966 A1* | 7/2004 | Ding | A61N 1/3627 | 607/9 |
| 2004/0193223 A1* | 9/2004 | Kramer | A61N 1/3627 | 607/9 |
| 2005/0038478 A1* | 2/2005 | Klepfer | A61N 1/3622 | 607/9 |
| 2005/0090870 A1* | 4/2005 | Hine | A61B 5/0422 | 607/17 |
| 2005/0149138 A1* | 7/2005 | Min | A61B 5/04012 | 607/27 |
| 2006/0247697 A1* | 11/2006 | Sharma | A61K 9/0019 | 607/9 |
| 2008/0004667 A1* | 1/2008 | Arcot-Krishnamurthy | A61N 1/36514 | 607/17 |
| 2008/0306567 A1* | 12/2008 | Park | A61N 1/36185 | 607/27 |
| 2009/0240301 A1* | 9/2009 | Dong | A61B 5/04525 | 607/28 |
| 2009/0254140 A1* | 10/2009 | Rosenberg | A61B 5/0422 | 607/17 |
| 2009/0299423 A1* | 12/2009 | Min | A61N 1/368 | 607/9 |
| 2010/0069987 A1* | 3/2010 | Min | A61N 1/3627 | 607/17 |
| 2010/0100145 A1* | 4/2010 | Min | A61N 1/3627 | 607/17 |
| 2010/0100148 A1* | 4/2010 | Min | G06F 19/00 | 607/17 |
| 2010/0204593 A1* | 8/2010 | Park | A61B 5/0537 | 600/508 |
| 2010/0262204 A1* | 10/2010 | McCabe | A61N 1/3627 | 607/17 |
| 2011/0022110 A1* | 1/2011 | Min | A61N 1/368 | 607/25 |
| 2011/0022112 A1* | 1/2011 | Min | A61N 1/3627 | 607/25 |
| 2011/0066201 A1* | 3/2011 | Rosenberg | A61B 5/042 | 607/17 |
| 2011/0066202 A1* | 3/2011 | Rosenberg | A61B 5/015 | 607/17 |
| 2011/0066203 A1* | 3/2011 | Rosenberg | A61B 5/042 | 607/17 |
| 2011/0098770 A1* | 4/2011 | Ryu | A61N 1/3627 | 607/25 |
| 2011/0098772 A1* | 4/2011 | Min | A61N 1/36185 | 607/28 |
| 2011/0319954 A1* | 12/2011 | Niazi | A61B 5/686 | 607/17 |
| 2012/0130303 A1* | 5/2012 | Sharma | A61K 9/0019 | 604/20 |

* cited by examiner

OPTIMAL PACING CONFIGURATION VIA VENTRICULAR CONDUCTION DELAYS

CROSS REFERENCE TO RELATED APPLICATIONS

This application is a divisional of co-pending U.S. patent application Ser. No. 12/632,519, filed Dec. 7, 2009, titled "Optima Pacing Configuration Via Ventricular Conduction Delays."

TECHNICAL FIELD

Subject matter presented herein relates generally to techniques for optimizing pacing therapies such as cardiac resynchronization therapy (CRT).

BACKGROUND

Cardiac resynchronization therapy (CRT) provides an electrical solution to the symptoms and other difficulties brought on by heart failure (HF). CRT can call for delivery of electrical stimuli to the heart in a manner that synchronizes contraction and enhances performance. When CRT delivers stimuli to the right and left ventricles, this is called biventricular pacing. Biventricular pacing aims to improve efficiency of each contraction of the heart and the amount of blood pumped to the body. This helps to lessen the symptoms of heart failure and, in many cases, helps to stop the progression of the disease.

CRT is typically administered via an implantable device such as a pacemaker (e.g., called a CRT-P) or an ICD that has a built-in pacemaker (e.g., called a CRT-D). A CRT-D has the added ability to defibrillate the heart if a patient is at risk for life-threatening arrhythmias. Most traditional ICDs or pacemakers have either one lead placed in the heart's right atrium (RA) or the heart's right ventricle (RV) or two leads where one is placed in the heart's RA and the other is placed in the heart's RV. CRT devices typically have three leads: one placed in the RA, one placed in the RV and one placed in a vein along the left ventricle (LV). Such a configuration allows for bi-ventricular pacing.

Some CRT devices are configured to connect to leads that have series of electrodes that can allow for more optimal delivery of pacing stimuli than leads with few electrodes (e.g., a lead with a tip electrode and a neighboring ring electrode). For example, a CRT platform marketed as the UNITY® platform (St. Jude Medical Corporation, Sylmar, Calif.) is configured for use with a so-called "quartet" LV lead having a quartet of LV electrodes. The UNITY® platform also includes a programmed optimization algorithm marketed as the QUICKOPT® algorithm (St. Jude Medical Corporation, Sylmar, Calif.) that can acquire data and optimize CRT based on the acquired data.

The QUICKOPT® algorithm can perform tests that acquire data and calculate one or more inter-ventricular conduction delays (inter-VCDs) for use in optimizing CRT. A specific inter-VCD is calculated as a difference between a delivery time for a stimulus delivered to one of the ventricles and a sensed activation time of a conducted wavefront responsive to the stimulus in the other ventricle. Such an inter-VCD may be referred to as a paced or stimulated RV-to-LV inter-VCD or a paced or stimulated LV-to-RV inter-VCD where delivery of a stimulus occurs using one ventricular lead (e.g., a LV or RV lead) and where sensing an activation time occurs using another ventricular lead (e.g., a RV or LV lead). Other types of inter-VCDs may be based on intrinsic activity (e.g., an intrinsic RV-to-LV inter-VCD or an intrinsic LV-to-RV inter-VCD). Inter-VCDs can be used for optimizing pacing delays for CRT (e.g., atrial to RV delay ($AV_{RV}$), atrial to LV delay ($AV_{LV}$) and/or inter-ventricular delay (VV).

As described herein, various exemplary techniques allow for optimization of lead and electrode configurations for delivery of cardiac therapies, including CRT, through use of conduction delays, optionally including inter-VCDs.

SUMMARY

An exemplary method for optimizing pacing configuration includes providing distances between electrodes of a series of three or more ventricular electrodes associated with a ventricle; selecting a ventricular electrode from the series; delivering energy to the ventricle via the selected ventricular electrode, the energy sufficient to cause an evoked response; acquiring signals of cardiac electrical activity associated with the evoked response via non-selected ventricular electrodes of the series; based on signals of cardiac electrical activity acquired via the non-selected ventricular electrodes and the distances, determining conduction velocities; based on the conduction velocities, deciding if the selected ventricular electrode is an optimal electrode for delivery of a cardiac pacing therapy; and, if the selected ventricular electrode comprises an optimal electrode for delivery of the cardiac pacing therapy, calling for delivery of the cardiac pacing therapy using the selected ventricular electrode. Various other methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the Implementations. The scope of the described implementations should be ascertained with reference to the issued claims. In the description that follows, like numerals or reference designators are generally used to reference like parts or elements throughout.

Overview

Various exemplary techniques described herein allow for CRT optimization in intraoperative, clinical or in vivo settings. In such settings, data are acquired and inter-ventricular conduction delays (inter-VCDs) calculated. Optimal CRT configurations, delivery parameters, etc., can then be determined based on an analysis of the inter-VCDs. In some examples, intra-VCDs may be analyzed in conjunction with inter-VCDs. In such examples, data acquisition for intra-VCDs optionally occurs through use of the QUICKOPT® algorithm. Various techniques may also acquire far-field ventricular signal data (e.g., via atrial electrodes, skin surface electrodes, etc.). Given such data, ventricular activation times and patterns may be estimated. Data may also be analyzed for indicia of functional block, which has proven more common where pacing stimuli emanate from multiple sites. As explained in more detail below, such exemplary techniques can effectively optimize CRT. Further, intra-VCDs may be calculated at various times over a period of months and analyzed to gain insight into progression of disease (e.g., congestive heart failure, condition of a chamber such as the left ventricle, etc.).

Exemplary Stimulation Device

Various techniques described below may be implemented in connection with a stimulation device that is configured or configurable to delivery cardiac therapy and/or sense information germane to cardiac therapy.

Figure 1:
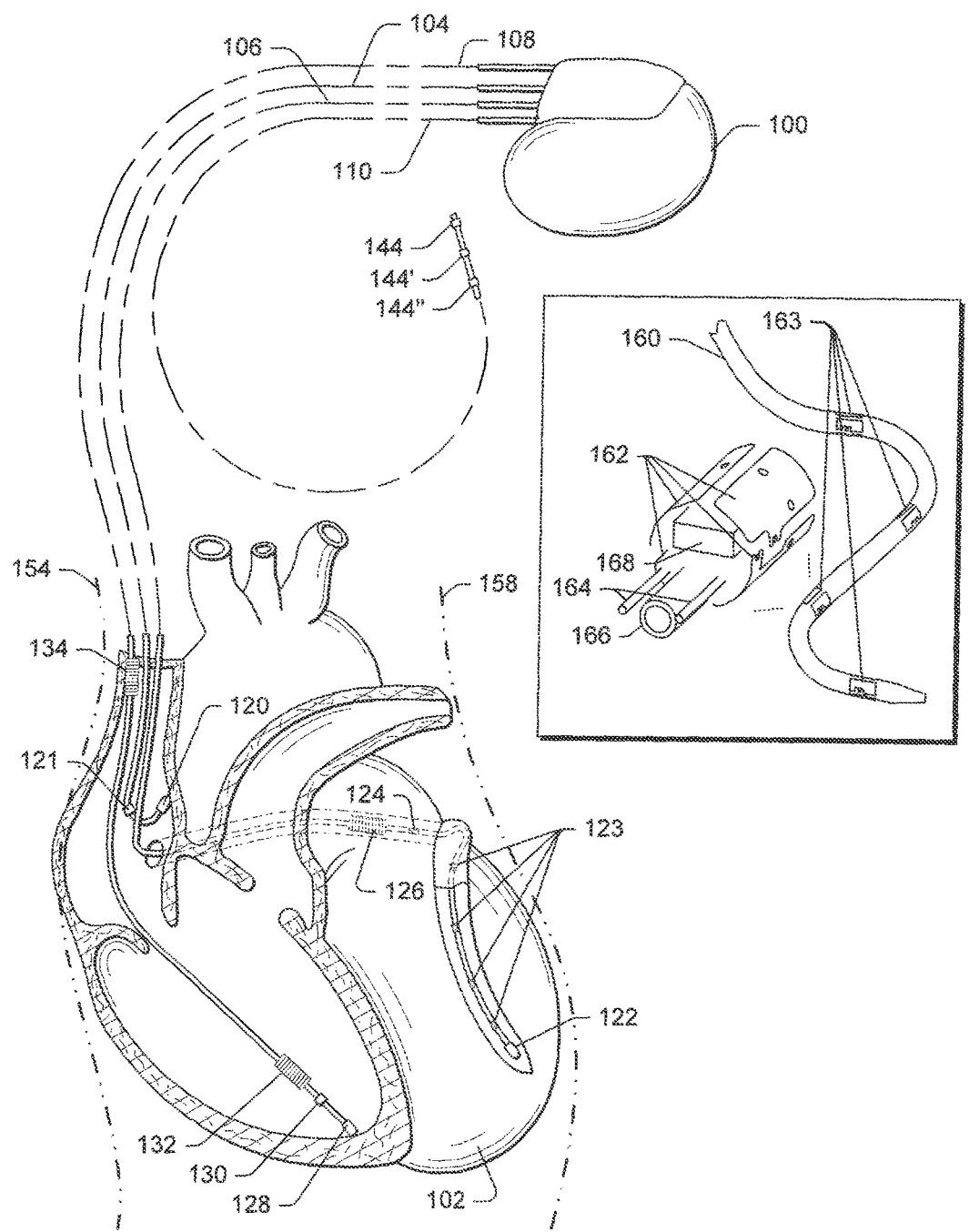
FIG. 1 is a simplified diagram illustrating an exemplary implantable stimulation device in electrical communication with at least three leads implanted into a patient's heart and at least one other lead for sensing and/or delivering stimulation and/or shock therapy. Approximate locations of the right and left phrenic nerves are also shown. Other devices with more or fewer leads may also be suitable for implementation of various exemplary techniques described herein.

FIG. 1 shows an exemplary stimulation device 100 in electrical communication with a patient's heart 102 by way of three leads (a right atrial lead 104, a left ventricular lead 106 and a right ventricular lead 108), suitable for delivering multi-chamber stimulation and shock therapy. The leads 104, 106, 108 are optionally configurable for delivery of stimulation pulses suitable for stimulation of nerves or other tissue. In addition, in the example of FIG. 1, the device 100 includes a fourth lead 110 having multiple electrodes 144, 144', 144" suitable for stimulation of tissue and/or sensing of physiologic signals. This lead may be positioned in and/or near a patient's heart and/or remote from the heart.

FIG. 1 also shows approximate locations of the right and left phrenic nerves 154, 158. The phrenic nerve is made up mostly of motor nerve fibers for producing contractions of the diaphragm. In addition, it provides sensory innervation for various components of the mediastinum and pleura, as well as the upper abdomen (e.g., liver and gall bladder). The right phrenic nerve 154 passes over the brachiocephalic artery, posterior to the subclavian vein, and then crosses the root of the right lung anteriorly and then leaves the thorax by passing through the vena cava hiatus opening in the diaphragm at the level of T8. More specifically, with respect to the heart, the right phrenic nerve 154 passes over the right atrium while the left phrenic nerve 158 passes over the pericardium of the left ventricle and pierces the diaphragm separately. While certain therapies may call for phrenic nerve stimulation (e.g., for treatment of sleep apnea), in general, cardiac pacing therapies avoid phrenic nerve stimulation through judicious lead and electrode placement, selection of electrode configurations, adjustment of pacing parameters, etc.

Referring again to the various leads of the device 100, the right atrial lead 104, as the name implies, is positioned in and/or passes through a patient's right atrium. The right atrial lead 104 is configured to sense atrial cardiac signals and/or to provide right atrial chamber stimulation therapy. As described further below, the right atrial lead 104 may be used by the device 100 to acquire far-field ventricular signal data. As shown in FIG. 1, the right atrial lead 104 includes an atrial tip electrode 120, which typically is implanted in the patient's right atrial appendage, and an atrial ring electrode 121. The right atrial lead 104 may have electrodes other than the tip 120 and ring 121 electrodes. Further, the right atrial lead 104 may include electrodes suitable for stimulation and/or sensing located on a branch.

To sense atrial cardiac signals, ventricular cardiac signals and/or to provide chamber pacing therapy, particularly on the left side of a patient's heart, the stimulation device 100 is coupled to the left ventricular lead 106, which in FIG. 1 is also referred to as a coronary sinus lead as it is designed for placement in the coronary sinus and/or tributary veins of the coronary sinus. As shown in FIG. 1, the coronary sinus lead 106 is configured to position at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method selects one or more electrodes (e.g., from electrodes 123 of the lead 106) and determines characteristics associated with conduction and/or timing in the heart to aid in ventricular pacing therapy and/or assessment of cardiac condition. As described in more detail below, an illustrative method acquires information using various electrode configurations where an electrode configuration typically includes at least one electrode of a coronary sinus lead or other type of left ventricular lead. Such information may be used to determine a suitable electrode configuration for the lead 106 (e.g., selection of one or more electrodes 123 of the lead 106).

In the example of FIG. 1, as connected to the device 100, the coronary sinus lead 106 is configured for acquisition of ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a particular coronary sinus lead, the reader is directed to U.S. Pat. No. 5,466,254, "Coronary Sinus Lead with Atrial Sensing Capability" (Helland), which is incorporated herein by reference.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108, as connected to the device 100, is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead. A right ventricular lead may include a series of electrodes, such as the series 123 of the left ventricular lead 106.

FIG. 1 also shows a lead 160 as including several electrode arrays 163. In the example of FIG. 1, each electrode array 163 of the lead 160 includes a series of electrodes 162 with an associated circuit 168. Conductors 164 provide an electrical supply and return for the circuit 168. The circuit 168 includes control logic sufficient to electrically connect the conductors 164 to one or more of the electrodes of the series 162. In the example of FIG. 1, the lead 160 includes a lumen 166 suitable for receipt of a guidewire to facilitate placement of the lead 160. As described herein, any of the leads 104, 106, 108 or 110 may include one or more electrode array, optionally configured as the electrode array 163 of the lead 160. In such arrangements, an exemplary method may include acquiring information and determining one or more intra-chamber conduction delays (e.g., a right intra-ventricular conduction delay, a left intra-ventricular conduction delay, a right intra-atrial conduction delay or a left intra-atrial conduction delay).

Figure 2:
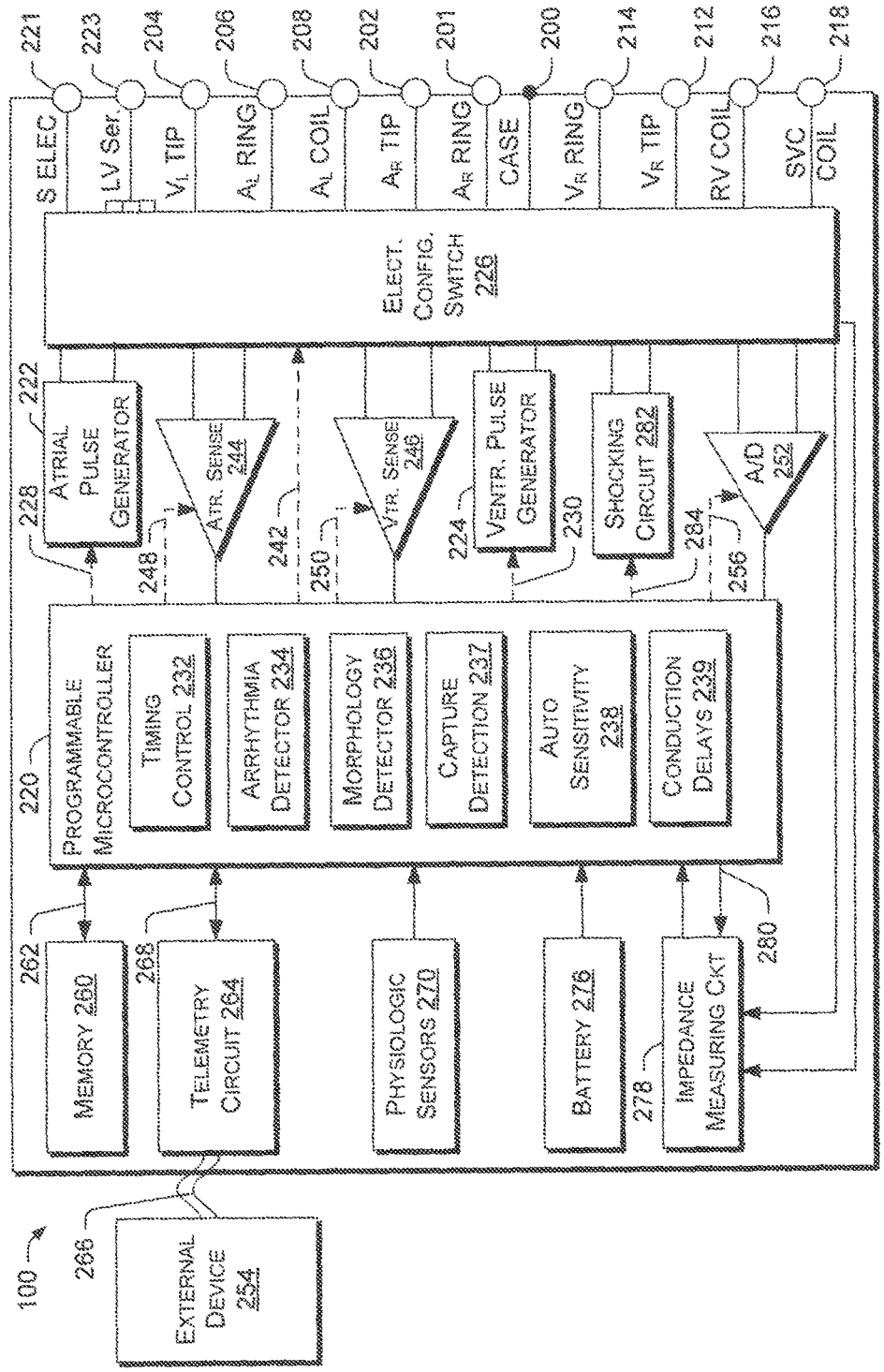
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of the device 100. The device 100 can be capable of treating both fast and slow arrhythmias with stimulation therapy, including cardioversion, defibrillation, and pacing stimulation. While a particular multi-chamber device is shown, it is to be appreciated and understood that this is for illustration purposes only. Thus, the techniques, methods, etc., described below can be implemented in connection with any suitably configured or configurable device. Accordingly, one of skill in the art could readily duplicate, eliminate, or disable the appropriate circuitry in any desired combination to provide a device capable of treating the appropriate chamber(s) or regions of a patient's heart.

Housing 200 for the device 100 is often referred to as the "can", "case" or "case electrode", and may be programmably selected to act as the return electrode for all "unipolar" modes. As described below, various exemplary techniques implement unipolar sensing for data that may include indicia of functional conduction block in myocardial tissue. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals).

To achieve right atrial sensing, pacing and/or other tissue sensing, stimulation, etc., the connector includes at least a right atrial tip terminal ($A_R$ TIP) 202 adapted for connection to the right atrial tip electrode 120. A right atrial ring terminal ($A_R$ RING) 201 is also shown, which is adapted for connection to the right atrial ring electrode 121. To achieve left chamber sensing, pacing, shocking, and/or other tissue sensing, stimulation, etc., the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

To support right chamber sensing, pacing, shocking, and/or other tissue sensing, stimulation, etc., the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their interrelationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

The microcontroller 220 further includes timing control circuitry 232 to control the timing of the stimulation pulses (e.g., pacing rate, atrio-ventricular (AV) delay, interatrial conduction (AA) delay, or interventricular conduction (W) delay, etc.) as well as to keep track of the timing of refractory periods, blanking intervals, noise detection windows, evoked response windows, alert intervals, marker channel timing, etc., which is well known in the art.

The microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The microcontroller 220 further includes a conduction delay module 239. The module 239 may be used to acquire data to calculate conduction delays, to calculate conduction delays, to analyze conduction delays, to optimize therapy based on one or more conduction delays, etc. The module 239 may operate in conjunction with a device other than the device 100 (internal or external). The microcontroller 220 may initiate one or more algorithms of the module 239 in response to a signal detected by various circuitry or information received via the telemetry circuit 264. Such a module may help monitor cardiac mechanics in relationship to cardiac electrical activity and, in turn, may help to optimize cardiac resynchronization therapy based at least in part on such monitoring. The module 239 may operate in conjunction with various other modules and/or circuits of the device 100 (e.g., the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each of the sensing circuits 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation) and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac signals are also applied to inputs of an analog-to-digital (A/D) data acquisition system 252. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or another lead (e.g., the lead 110) through the switch 226 to sample cardiac signals or other signals across any pair or other number of desired electrodes. A control signal 256 from the microcontroller 220 may instruct the A/D 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming and operation of the device 100.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, VV Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, oxygen concentration of blood, pH of blood, $CO_2$ concentration of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 which is hereby incorporated by reference.

The one or more physiologic sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 $cm^2$) and/or higher current frequencies (e.g., above about 10 kHz) to reduce noise.

Figure 3:
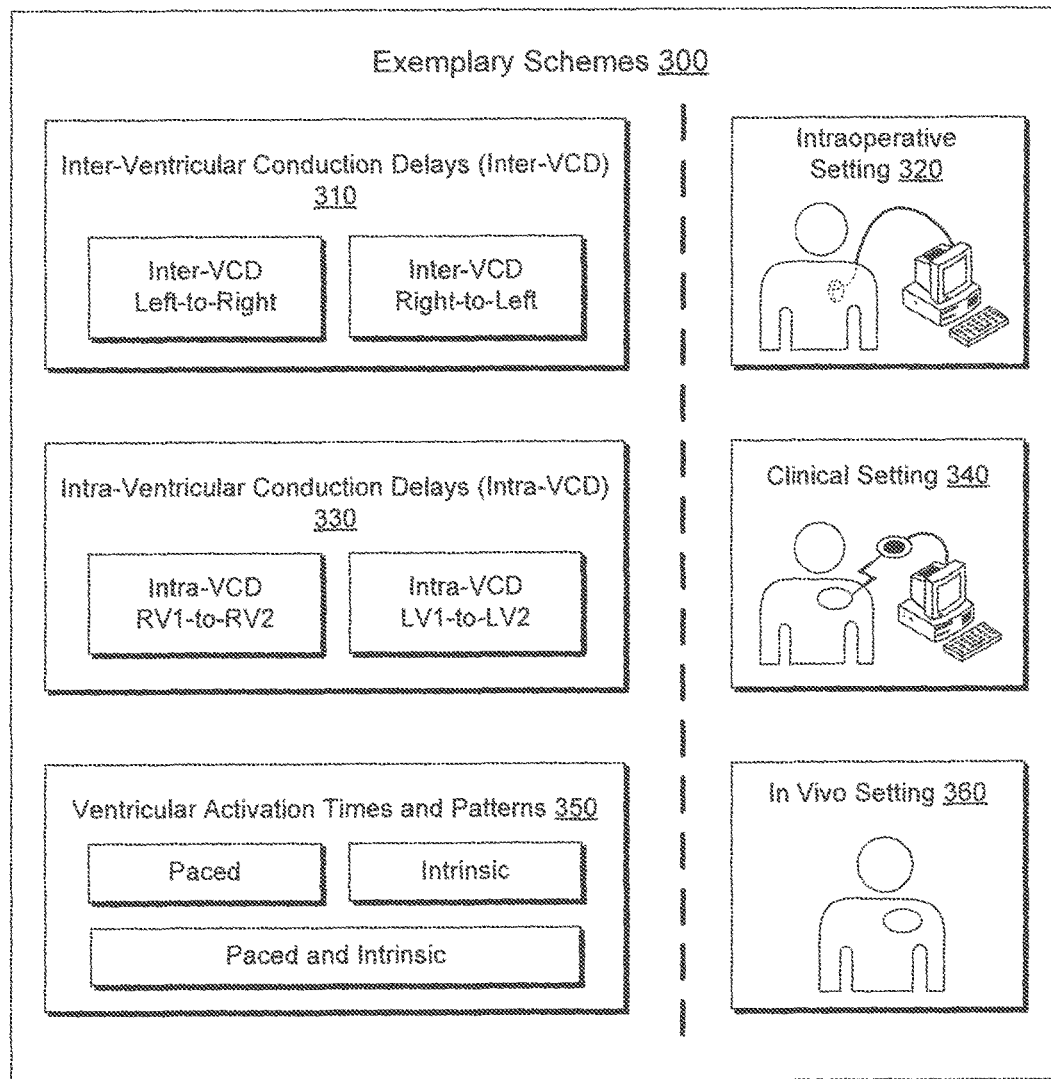
FIG. 3 is a block diagram of various exemplary schemes suitable for implementation in an intraoperative setting, a clinical setting or an in vivo setting.

FIG. 3 shows exemplary schemes 300 as corresponding to types of information acquired or analyzed and types of settings. The types of information include inter-VCDs 310, which may be from left ventricle to right ventricle or right ventricle to left ventricle, intra-VCDs 330, which may be for the right ventricle or the left ventricle, and ventricular activation times and patterns 350, which may be based on data acquired as associated with delivery of stimuli to the heart (e.g., pacing stimuli), data acquired as associated with intrinsic activation of the heart or a combination of both paced and intrinsic. The types of settings include intraoperative 320, which involves an invasive procedure such as placing a catheter or lead in the body and acquiring signals from the catheter or lead, clinical 340, which involves telemetric communication between an implanted device and an external device, and in vivo 360, which involves an implanted device only.

As described herein, various techniques can be implemented in one or more of the settings, for example, depending on device configuration and whether a technique requires involvement of a clinician. With respect to the intraoperative setting 320, a clinician may navigate a catheter or lead in a body of a patient and acquire data using an external computing device. In this example, the computing device may include algorithms to calculate inter-VCDs 310, intra-VCDs 330 or other information and determine ventricular activation times and patterns 350. Such determinations may then allow the clinician to appropriately position one or more leads (or electrodes thereof) for optimal delivery of CRT.

With respect to the clinical setting 340, a clinician may instruct an implanted device to perform one or more tests to acquire data. Once acquired, the data may be communicated to an external computing device for analysis. In this example, the external computing device may include algorithms to calculate inter-VCDs 310, intra-VCDs 330 or other information and determine ventricular activation times and patterns 350. Such determinations may then allow the clinician to appropriately select one or more electrodes, pacing parameters, etc., for optimal delivery of CRT.

With respect to the in vivo setting 360, an implanted device may be programmed to perform one or more tests to acquire data (e.g., according to a schedule, an event, a condition, etc.). Once acquired, the data may be analyzed by the implanted device via one or more algorithms to calculate inter-VCDs 310, intra-VCDs 330 or other information and determine ventricular activation times and patterns 350. Such determinations may then allow the implanted device to appropriately select one or more electrodes, pacing parameters, etc., for optimal delivery of CRT.

As described herein, an exemplary method includes acquiring data (e.g., using electrodes of a LV lead, optionally with electrode arrays per the lead 160 of FIG. 1), calculating local intra-VCDs based on the acquired data and optimizing therapy based in part or wholly on such local intra-VCDs. Another exemplary method includes acquiring far-field ventricular signal data (e.g., atrial, surface ECG, etc.) and estimating ventricular activation times, patterns or a combination thereof from far-field activation events, durations, morphology, etc.

As described herein, an exemplary method includes acquisition of data and calculation of local intra-VCDs is accomplished during a QUICKOPT® algorithm sense/pace test (e.g., RV pace to LV (all electrodes) sense, LV (individual electrode) pace to RV sense, etc.). In this example, the QUICKOPT® algorithm may be modified to include intra-VCD tests or inter-VCD results of the QUICKOPT® algorithm may be combined with intra-VCD results to optimize CRT.

As described herein, an exemplary method includes estimation of ventricular activation time/pattern through monitoring far-field ventricular activation as sensed from a right atrial lead, a coronary sinus electrodes located at or near the left atrium (e.g., proximal electrodes of a multipolar LV lead or a dedicated left atrial lead) or monitoring QRS duration/morphology changes from an ECG device (e.g., optionally during a QUICKOPT® inter-VCD test).

Referring again to the settings 320, 340 and 360, in general, for the intraoperative setting 320, lead or electrode configurations include those achievable by physically re-positioning a lead in a patient's body. In contrast, the settings 340 and 360 may be considered as allowing only chronic configurations, which normally do not allow for re-positioning as a lead or leads are usually anchored during implantation or become anchored in the weeks to months after implantation. Chronic configurations do, however, include selection of a subset of the multiple implanted electrodes, for example using a tip electrode versus a particular ring electrode as a cathode or using the tip electrode and a ring electrode as a bipolar pair versus using the tip electrode and the ring electrode as two independent cathodes. Thus, intra-operative configurations include configurations available by changing device settings, electrode selection, and physical position of electrodes, while chronic configurations include only those configurations available by changing device settings and electrode selection, or "electronic repositioning" of one or more stimulation electrodes.

As described herein, information acquired via one or more of the exemplary schemes 300 of FIG. 3 may be used to diagnose cardiac condition. For example, intra-VCDs may be calculated at various times over a period of months and analyzed to gain insight into progression of disease (e.g., congestive heart failure, condition of a chamber such as the left ventricle, etc.). In such an example, inter-VCDs may be used in conjunction with intra-VCDs, which may allow for discernment between local and global cardiac health (e.g., right ventricular health, left ventricular health or global ventricular health).

Figure 4:
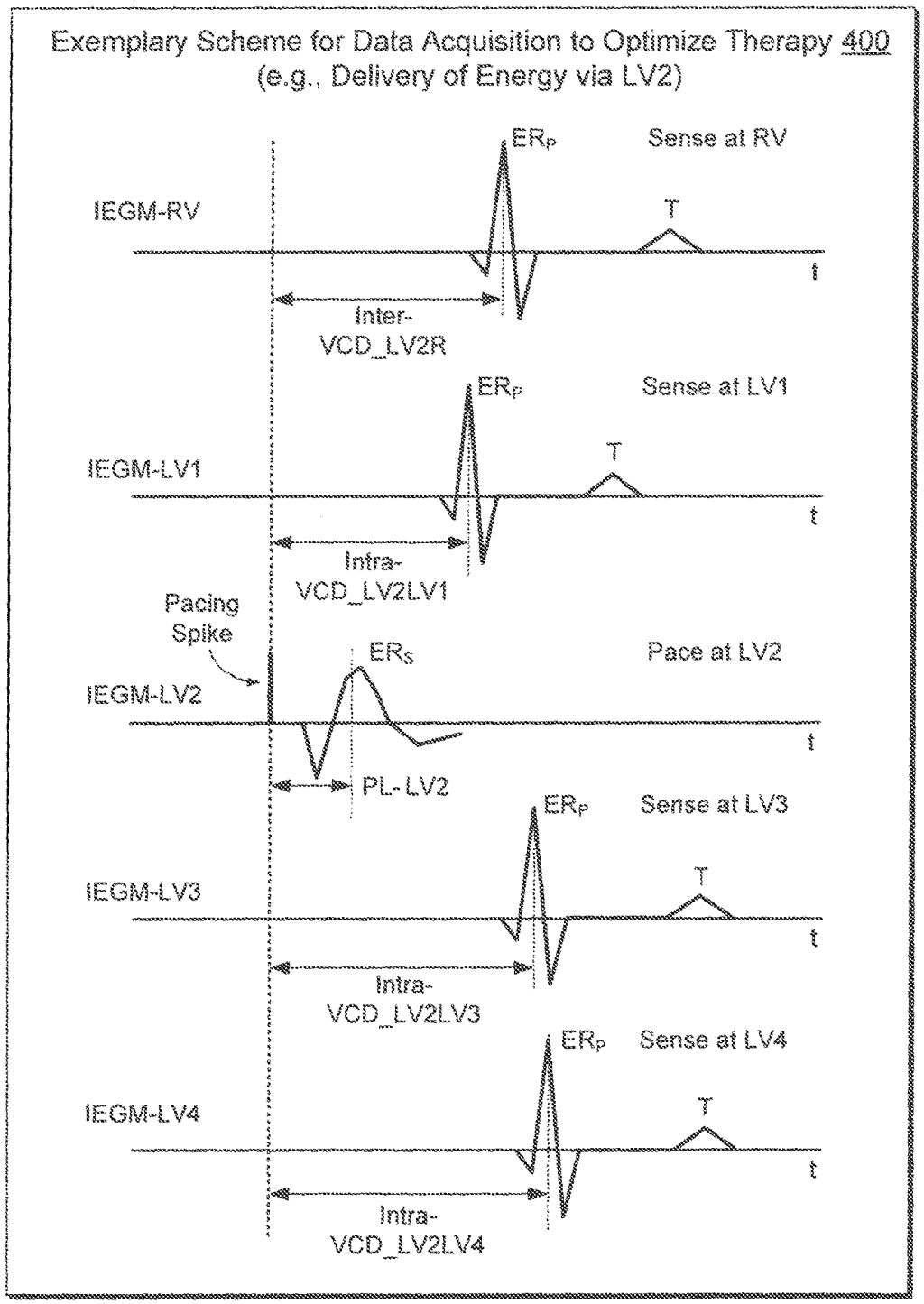
FIG. 4 is a diagram of various IEGMs representative of data acquired to calculate one or more intra-ventricular conduction delays.

FIG. 4 shows an exemplary scheme 400 for data acquisition to optimize therapy. The scheme 400 shows various IEGM signals as acquired via a right ventricular lead (IEGM-RV) and a left ventricular lead (IEGM-LV1, LV2, LV3 and LV4). The scheme 400 may be implemented in an intraoperative setting, a clinical setting or an in vivo setting. Specifically, FIG. 4 shows a particular portion of the scheme 400 where a pacing stimulus is delivered to the heart using one of a series of left ventricular electrodes. For example, consider the series of electrodes 123 shown in FIG. 1 where the second electrode (denoted LV2) in the series is selected and used to delivery energy to the heart (e.g., in combination with another electrode in a unipolar or multipolar arrangement).

According to the IEGM-LV2, the energy delivered to the heart (shown as a pacing spike at a delivery time) is sufficient to cause an evoked response (ERs). The IEGM-LV2 may be analyzed to determine a pacing latency, which may be defined as the time delay between the delivery time and a time corresponding to a point of the evoked response waveform (ERs). As described herein, pacing latency, as a delay, may be used for optimizing therapy.

In the scheme 400, data sufficient to determine three intra-VCDs are acquired along with data sufficient to determine an inter-VCD. Specifically, the IEGM-LV1, IEGM-LV3 and IEGM-LV4 provide for calculation of respective intra-VCDs while the IEGM-RV provides for calculation of an inter-VCD where stimulus energy is delivered, at least in part, via the electrode LV2 of the series of electrodes LV1, LV2, LV3 and LV4. The IEGMs for LV1, LV3 and LV4 show the respective intra-VCDs calculated as the difference between a time associated with the sensed activation waveform and the time of delivery of the pacing stimulus while the IEGM-R shows the inter-VCD calculated as the difference between a time associated with the sensed activation waveform in the right ventricle and the time of delivery of the pacing stimulus to the left ventricle (i.e., a left-to-right inter-VCD). Such an analysis of the IEGMs provides insight into the local conduction environment (intra-VCDs) and a more global conduction environment (inter-VCD). Where repeated for LV1, LV3 and LV4, a more complete understanding emerges as to the local conduction environment and global conduction environment.

As to particular techniques to denote a time or times of an activation wavefront, an exemplary method may rely on time of onset of a peak (e.g., deviation from a baseline value), time of maximum peak, time of maximum derivative of signal potential with respect to time, time of minimum derivative of signal potential with respect to time, time of maximum second derivative of potential with respect to time, time of minimum second derivative of potential with respect to time, or time of end of a peak.

As described herein, various metrics may be determined based on denoted times or delays. For example, intra-VCDs for a particular paced electrode may be summed and divided by the sum of the distances between the paced electrode and the sensing electrodes to provide an average conduction time (s/mm) whereas the inverse provides an average conduction velocity (mm/s). An averaged conduction delay may be determined, alternatively, as the sum of the conduction delays (i.e., sum of the intra-VCDs) divided by the number of sensing sites (s/site). For any of the metrics, standard deviation may be calculated and relied on to decide whether a site is optimal. For example, an exemplary method may select a pacing site that produces the minimum average conduction delay, the maximum average conduction velocity or the minimum standard deviation as an optimal pacing site.

Figure 5:
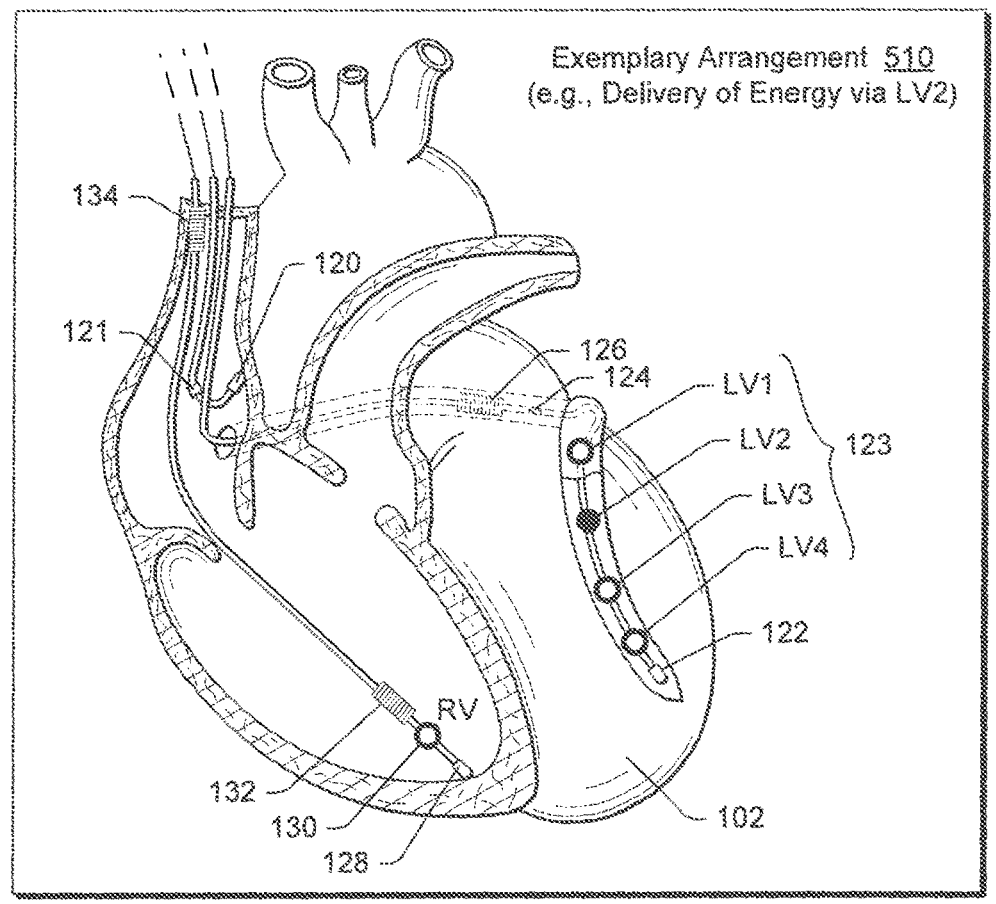
FIG. 5 is a diagram of an exemplary arrangement of leads and electrodes for acquiring data and exemplary data and metrics based on the acquired data.

FIG. 5 shows an exemplary arrangement 510 and exemplary data and metrics 530. The exemplary arrangement 510 corresponds to the scheme 400 of FIG. 4 where energy is delivered to the left ventricle via the LV2 electrode and where IEGMs are acquired using the LV1, LV3, LV4 and RV electrodes. The exemplary data and metrics 530 include pacing latency, distance between the LV2 and other electrodes (if known), time delay and conduction velocity. The numbers provided are for purposes of illustration as actual numbers will depend on any of a variety of factors.

In the example of FIG. 5, the distances between the electrodes LV1, LV2, LV3 and LV4 are known as is the distance between the LV2 electrode and the RV electrode 130. Based on the distance information and the measured delays, conduction velocities are calculated. As described herein, the conduction velocities for the series of electrodes 123 are referred to as local conduction velocities. Depending on the circumstances, the distance between the LV2 and the RV electrode may not be known or known with less accuracy than the distances between the electrodes of the series 123, which are all on the same lead. Even though the distance to an electrode on a different lead may not be known with great accuracy (e.g., not known to within 50 mm), a distance may be used for purposes of comparison where tests are performed using each of the LV electrodes of the series 123.

Figure 6:
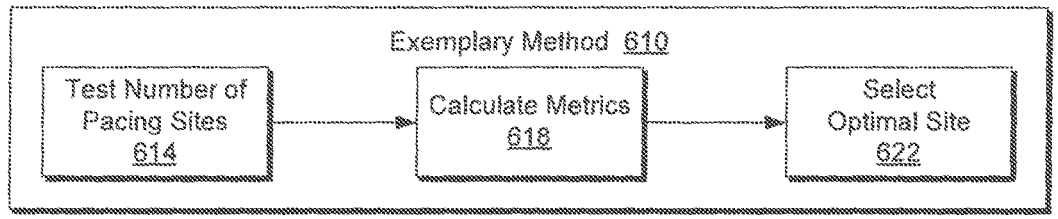
FIG. 6 is a diagram of an exemplary scenario for optimizing configuration of a device for delivery of cardiac therapy based on various metrics.
Figure 6:
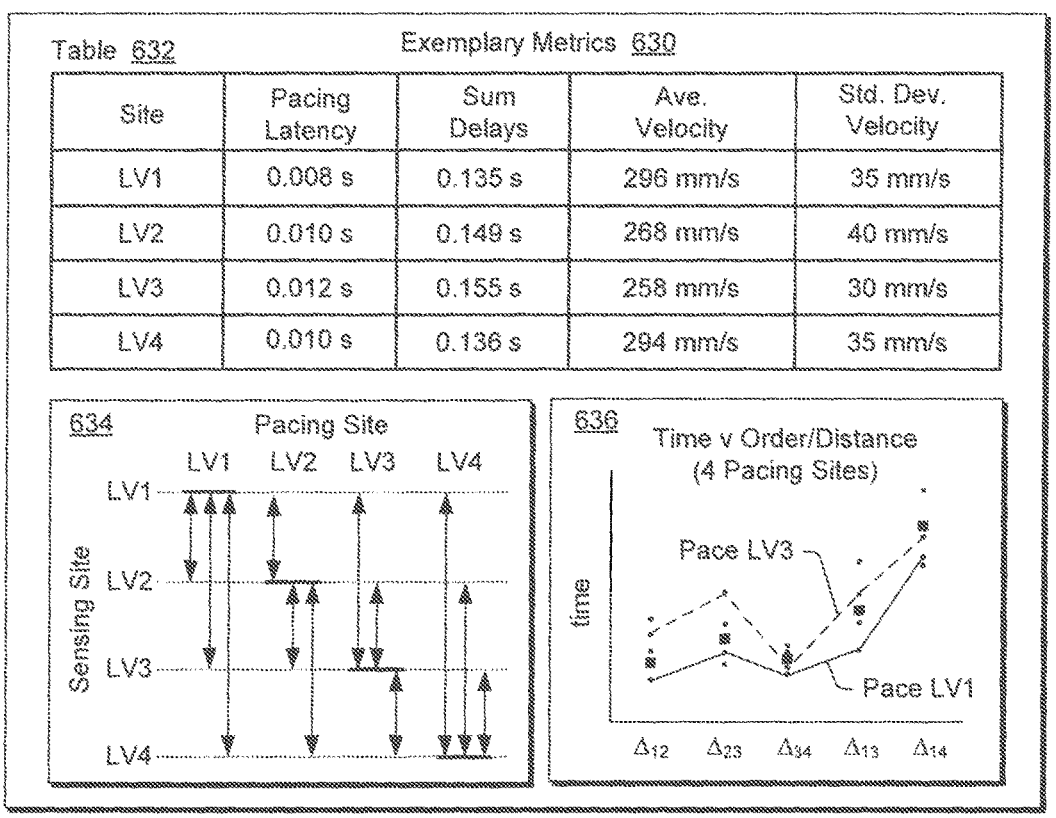
Figure 6:
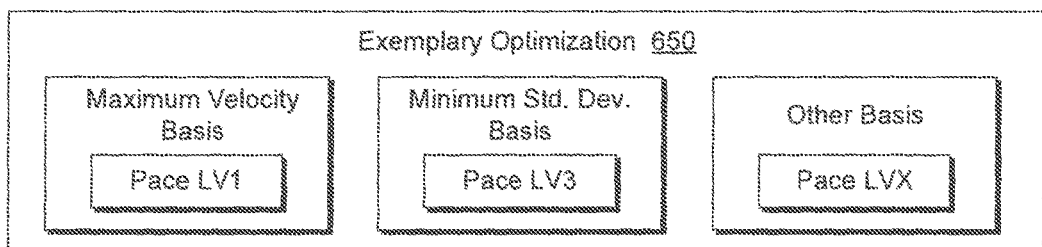

FIG. 6 shows an exemplary scenario 600 corresponding to a method 610 where delivery of energy occurs for each of four LV electrodes. The method 610 includes a test block 614 that calls for testing a number of pacing sites. After testing, a calculation block 618 calls for calculating various metrics. A selection block 622 follows that selects an optimal site based on the calculated metrics.

For purposes of illustration, exemplary metrics 630 are shown in FIG. 6, for example, as calculated per the calculation block 618. The metrics 630 include a table 632 of pacing latency, a sum of delays, average conduction velocity and standard deviation of the conduction velocity; various time differentials ($\Delta_{12}$, $\Delta_{23}$, $\Delta_{34}$, $\Delta_{14}$ and $\Delta_{13}$) 634 based on distances between four electrodes; and a plot 636 of the time differentials for the four electrodes. In the plot 636, squares mark the average time differential based on differentials measured where each electrode is paced. Where each of four electrodes is paced, three differential times can be measured and two additional differential times can be calculated (e.g., as a difference of two times). Thus, the plot 636 includes four differential times for each of $\Delta_{12}$, $\Delta_{23}$, $\Delta_{34}$, $\Delta_{14}$ and $\Delta_{13}$. In the example of FIG. 6, a solid line connects times associated with LV1 and a dashed line connects times associated with LV3. A comparison may be made between the lines to determine which pacing site results in shorter times and hence higher conduction velocities. Such data may be tracked with respect to time, for example, to aid in diagnosis of one or more issues (e.g., changes in condition, localization of changes, changes in electrodes, changes in interface between an electrode and the heart, etc.). For example, if one of the differentials increases with respect to time while other differentials remain relatively constant, an issue may exist. A comparison with one or more differentials may indicate the nature of the issue (e.g., myocardial, electrode, etc.).

An exemplary optimization 650 aims to select, per the selection block 622, the optimal site for delivery of pacing energy to the left ventricle of the heart. If the optimization 650 relies on maximum average conduction velocity or the plot 636, then the site LV1 will be selected. However, if the optimization 650 relies on minimum standard deviation as a basis, then site LV3 will be selected (e.g., even though the line for LV3 in the plot 636 indicates longer times). Any of a variety of bases may be used where the choice of a particular basis may depend on how well a patient responds to optimization according to that basis. For example, if a patient responds favorably to a optimal site selected on the basis of minimum sum of delays, then that basis may be chosen for use in the method 610 (e.g., for the calculation block 618 and the selection block 622).

Figure 7:
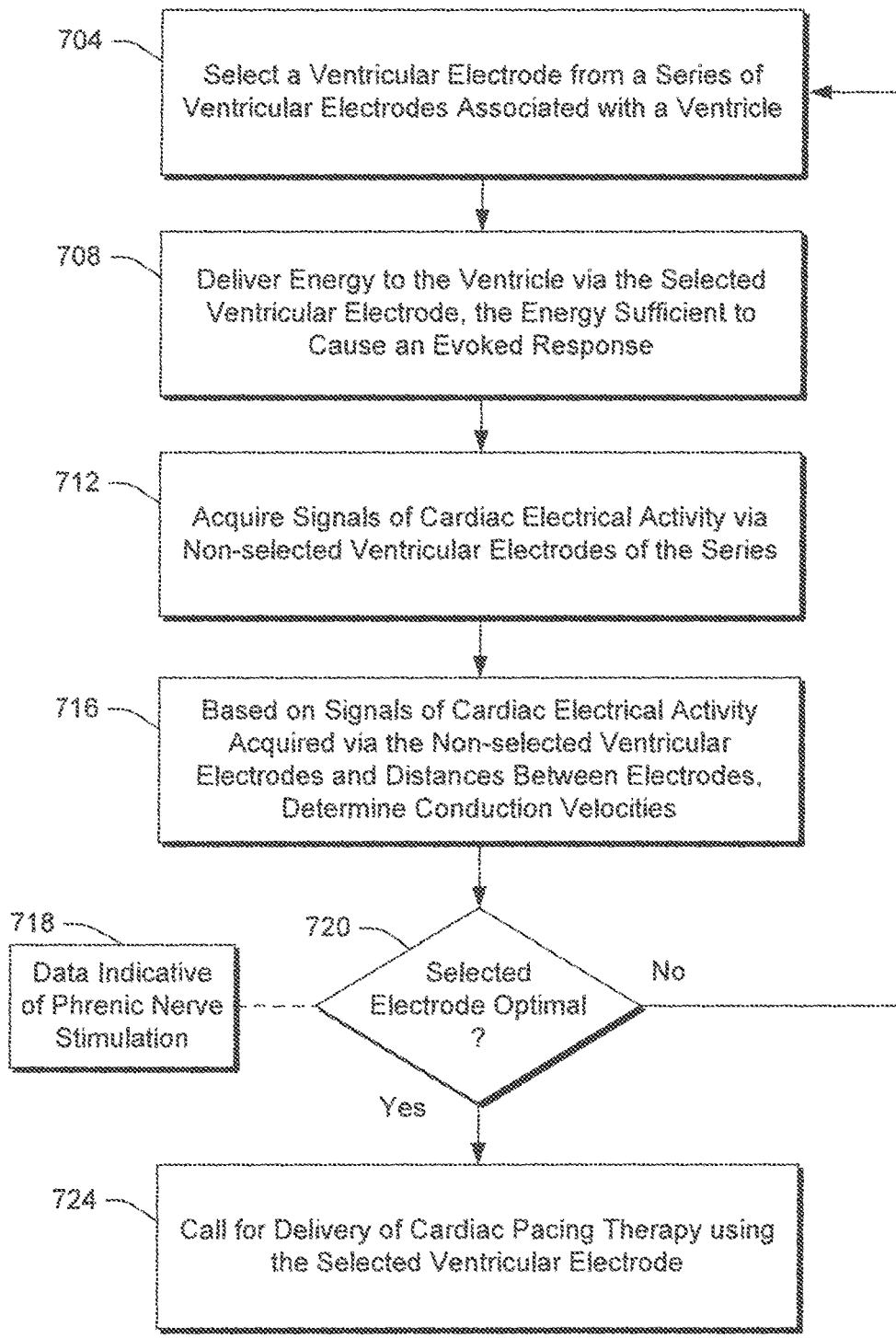
FIG. 7 is a block diagram of an exemplary method for optimizing a cardiac pacing therapy based at least in part on one or more intra-ventricular conduction velocities.

FIG. 7 shows an exemplary method 700 for optimizing a cardiac pacing therapy. The method 700 includes a selection block 704 for selecting a ventricular electrode from a series of electrodes (e.g., a series of three or more electrodes). Such a selection may occur in any one of the three settings shown in FIG. 3 (i.e., intraoperative, clinical or in vivo). After selection, the method 700 includes a delivery block 708 for delivering energy to a ventricle via the selected ventricular electrode, the energy sufficient to cause an evoked response. An acquisition block 712 provides for acquiring signals of cardiac electrical activity associated with the evoked response via non-selected ventricular electrodes of the series. A determination block 716 provides for, based on signals of cardiac electrical activity acquired via the non-selected ventricular electrodes and the distances, determining conduction velocities. In this example, distances between the electrodes of the series may be known or otherwise provided a priori. According to the method 700, a decision block 720 follows that, based on the conduction velocities, provides for deciding if the selected ventricular electrode is an optimal electrode for delivery of a cardiac pacing therapy. As shown in FIG. 7, an input block 718 may input additional information such as whether phrenic nerve stimulation occurred, which would possibly preclude the selected electrode from being an optimal electrode. In the instance that the decision block 720 decides that the selected ventricular electrode is an optimal electrode for delivery of the cardiac pacing therapy, the method 700 proceeds to a call block 724 includes calling for delivery of the cardiac pacing therapy using the selected ventricular electrode.

In the instance that the decision block 720 decides that the selected electrode is not an optimal electrode for delivery of the cardiac pacing therapy, the method 700 includes repeating the selecting of the selection block 704 to select a different ventricular electrode from the series and repeating the various blocks 708, 712, 716 and 720 to perform the corresponding delivering, acquiring, determining and deciding for the selected, different ventricular electrode.

The exemplary method 700 may determine conduction velocities, for each of the non-selected ventricular electrodes, by dividing the distance between the non-selected ventricular electrode and the selected ventricular electrode by an intra-ventricular conduction delay, as explained with respect to FIGS. 4, 5 and 6. For example, the intra-ventricular conduction delay for the non-selected electrode may be calculated as a difference between a delivery time for the delivered energy and an evoked response time based on signals of cardiac electrical activity acquired via the non-selected. Further, as mentioned with respect to FIGS. 4, 5 and 6, one or more pacing latencies may be determined by acquiring signals of cardiac electrical activity via a selected ventricular electrode and, based on signals of cardiac electrical activity acquired via the selected ventricular electrode, determining a pacing latency as corresponding to the selected electrode.

As described herein, an exemplary method may include deciding whether an electrode is optimal based on conduction velocities and at least in part on a pacing latency associated with the selected ventricular electrode. As explained with respect to FIGS. 4 and 5, an exemplary method can include acquiring signals of cardiac electrical activity associated with an evoked response corresponding to a stimulus delivered to one ventricle via a ventricular electrode associated with the other ventricle. In such a method, a decision block may decide whether an electrode is optimal based on conduction velocities and at least in part on signals of cardiac electrical activity acquired via the ventricular electrode associated with the other ventricle. Such a method may include determining an inter-ventricular conduction delay based at least in part on signals of cardiac electrical activity acquired via the ventricular electrode associated with the other ventricle.

An exemplary method, such as the method 700, may include an acquisition block that provides for acquiring signals of cardiac electrical activity via an atrial electrode. In such a method, a decision block may decide whether an electrode is optimal based on conduction velocities and at least in part on signals of cardiac electrical activity acquired via the atrial electrode.

As explained with respect to FIG. 6, an exemplary method can include deciding whether an electrode is optimal based on a sum of the conduction velocities, for example, by determining if the sum for the selected ventricular electrode is less than a sum corresponding to another ventricular electrode of the series. Another approach may include deciding based on a standard deviation of the conduction velocities, for example, where the electrode is deemed optimal if the standard deviation for the selected ventricular electrode is less than a standard deviation corresponding to another ventricular electrode of the series.

As mentioned, at times, pacing can cause functional conduction block. Accordingly, an exemplary method may include analyzing signals of cardiac electrical activity acquired via non-selected ventricular electrodes for indicia of functional conduction block. Such a method typically acquires signals of cardiac electrical activity using unipolar sensing (e.g., unipolar signals). As described in more detail below, indicia of functional conduction block includes split potentials.

An exemplary implantable device suitable for implementing the method 700 of FIG. 7 or aforementioned variants thereof includes a connector for connecting a lead that has a series of three or more ventricular electrodes associated with a ventricle; control logic for selecting a ventricular electrode from the series; control logic for delivering energy to the ventricle via the selected ventricular electrode, the energy sufficient to cause an evoked response; control logic for acquiring signals of cardiac electrical activity via non-selected ventricular electrodes of the series; control logic for, based on signals of cardiac electrical activity acquired via the non-selected ventricular electrodes and distances between the ventricular electrodes of the series, determining conduction velocities; control logic for, based on the conduction velocities, deciding if the selected ventricular electrode is an optimal electrode for delivery of a cardiac pacing therapy; and control logic for, if the selected ventricular electrode comprises an optimal electrode for delivery of the cardiac pacing therapy, calling for delivery of the cardiac pacing therapy using the selected ventricular electrode. As described herein, control logic may be implemented using hardware or software instructions for execution on hardware (e.g., a microprocessor such as the microprocessor 220 of FIG. 2).

As described herein, an exemplary method may include diagnosing cardiac condition based at least in part on one or more conduction velocities and optionally one or more previously determined conduction velocities (e.g., one or more stored conduction velocities). An exemplary method may include determining an intra-ventricular conduction delay and diagnosing cardiac condition based at least in part on the intra-ventricular conduction delay and optionally one or more previously determined intra-ventricular conduction delays. An exemplary device may be configured to store previously acquired information or determined metrics (e.g., conduction velocities, delays, etc.) and to diagnose cardiac condition based at least in part on such stored information.

Figure 8:
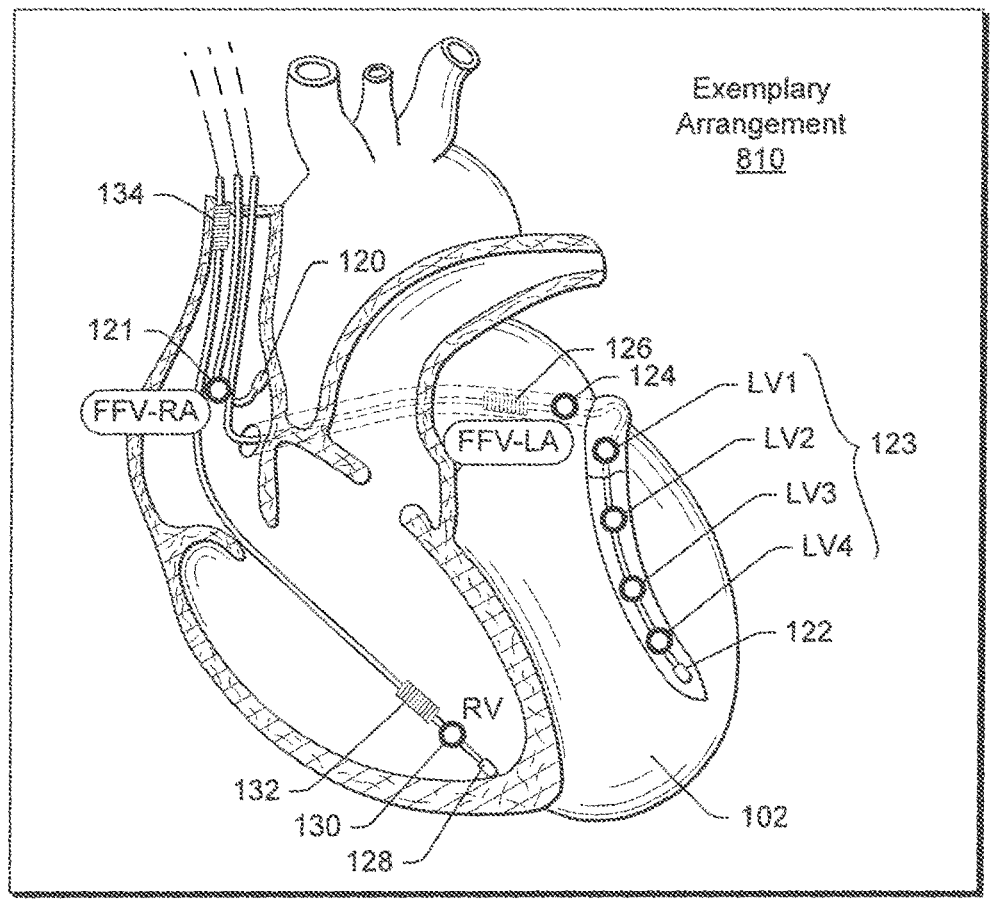
FIG. 8 is a diagram of an exemplary arrangement of leads and electrodes for acquiring data and exemplary data acquired using the arrangement.

FIG. 8 shows an exemplary arrangement 810 and corresponding exemplary delays 830 based on data acquired using the arrangement 810. The arrangement 810 includes various leads and electrodes as shown in the arrangement 510 of FIG. 5. However, in FIG. 8, the "atrial" electrodes 121 and 124 are labeled as being configured to sense far-field ventricular signals (i.e., right atrial far-field ventricular sensing (FFV-RA) and left atrial far-field ventricular sensing (FFV-LA)). The exemplary delays 830 are for purposes of illustration as such delays would depend on a variety of factors, which may be specific to a patient, a device, arrangement of device and electrodes, electrode type, etc.

The exemplary delays 830 represent information acquired or otherwise determined according to an exemplary method that includes delivery of energy using an electrode (e.g., in combination with one or more other electrodes) and sensing cardiac activity using at least some other electrodes. For example, where energy is delivered by a selected electrode, using the electrode LV1 as an example, data are acquired sufficient to calculate the following metrics: delay from LV1 site to RV site, delay from LV1 site to right atrial site (FFV-RA), delay from LV1 site to left atrial site (FFV-LA), delay from LV1 site to LV2, LV3 and LV4 sites, pacing delay for site LV1 and optionally delay from LV1 site to a surface ECG recording (e.g., to a QRS waveform).

As described herein, the foregoing delays or activation times can be used to understand local activation, global activation and patterns of activation, which can be used to optimize therapy. For example, an exemplary method can acquire data to determine delays such as the delays 830. Specifically, the FFV-RA delay may be analyzed as representative of right ventricular basal activation and the FFV-LA delay may be analyzed as representative of left ventricular lateral basal activation.

Calculation of activation time for a far-field activation wavefront can be based on a delivery time or other marker as a start time and, as an end time, a time of onset of a peak (e.g., deviation from a baseline value), time of maximum peak, time of maximum derivative of signal potential with respect to time, time of minimum derivative of signal potential with respect to time, time of maximum second derivative of potential with respect to time, time of minimum second derivative of potential with respect to time, or time of end of a peak. In various examples, a skin surface electrode ECG waveform may be analyzed to provide a measure of a global activation time corresponding to energy delivered via a selected electrode.

As described herein, an exemplary method includes acquiring data and calculating various delays such as those shown in FIG. 8. Such a method may estimate a total ventricular activation time as the longest of the calculated time delays for a particular pacing electrode. Such a method may estimate a left ventricular activation time as the longest of, for example, the FFV-LA and LV1-LV2, LV1-LV3 and LV1-LV4 delays for the electrode LV1 (similarly for other LV electrodes). Such a method may estimate a right ventricular activation time as a difference between LV1-RV and FFV-RA for the electrode LV1 (similarly for other LV electrodes). Further, an exemplary method may include determining whether, for an energy delivery electrode LVx, a LVx to RV delay is greater than FFV-RA, FFV-LA and/or QRS-ECG delays for LVx. If so, then the method may conclude that the conduction path from LVx electrode to the RV sensing site is likely have some degree of conduction abnormalities. Accordingly, the method may exclude the LVx site from consideration as an optimal LV site and optionally call for testing of different pacing configuration(s) to improve conduction of wavefronts between these electrodes.

Given the arrangement 810, when energy delivery occurs via a RV electrode, the LV and RV activation times will be estimated accordingly to account for differences, however, the total ventricular activation time can be estimate in the same manner as for the LV example. For delivery of energy via an RV electrode, the LV activation time can be estimated from as the latest time of RV-LV1, LV2, LV3 or LV4 minus FFV-LA; whereas, the RV activation time can be estimated from FFV-RA.

As described herein, an exemplary method includes acquiring information via all possible or selected pacing sites and pacing configurations at each pacing site and optimizing a pacing therapy based on an analysis of the information. As described herein, total ventricular activation time, LV activation time, and/or RV activation time can be estimated during intrinsic rhythm in a manner akin to that for the artificially stimulated examples.

As to optimal selection of a pacing site, for the left ventricle site selection criteria can include: the site with a minimum average conduction time, a minimum standard deviation of the conduction time, a maximum average velocity, and/or a minimum standard deviation of velocity. Once selected, an exemplary method can including verifying whether the selected site (e.g., LVx) is optimal by checking the inter-VCD (e.g., LVx to RV) to see if a functional block exists between the sites (e.g., LVx and RV).

Figure 9:
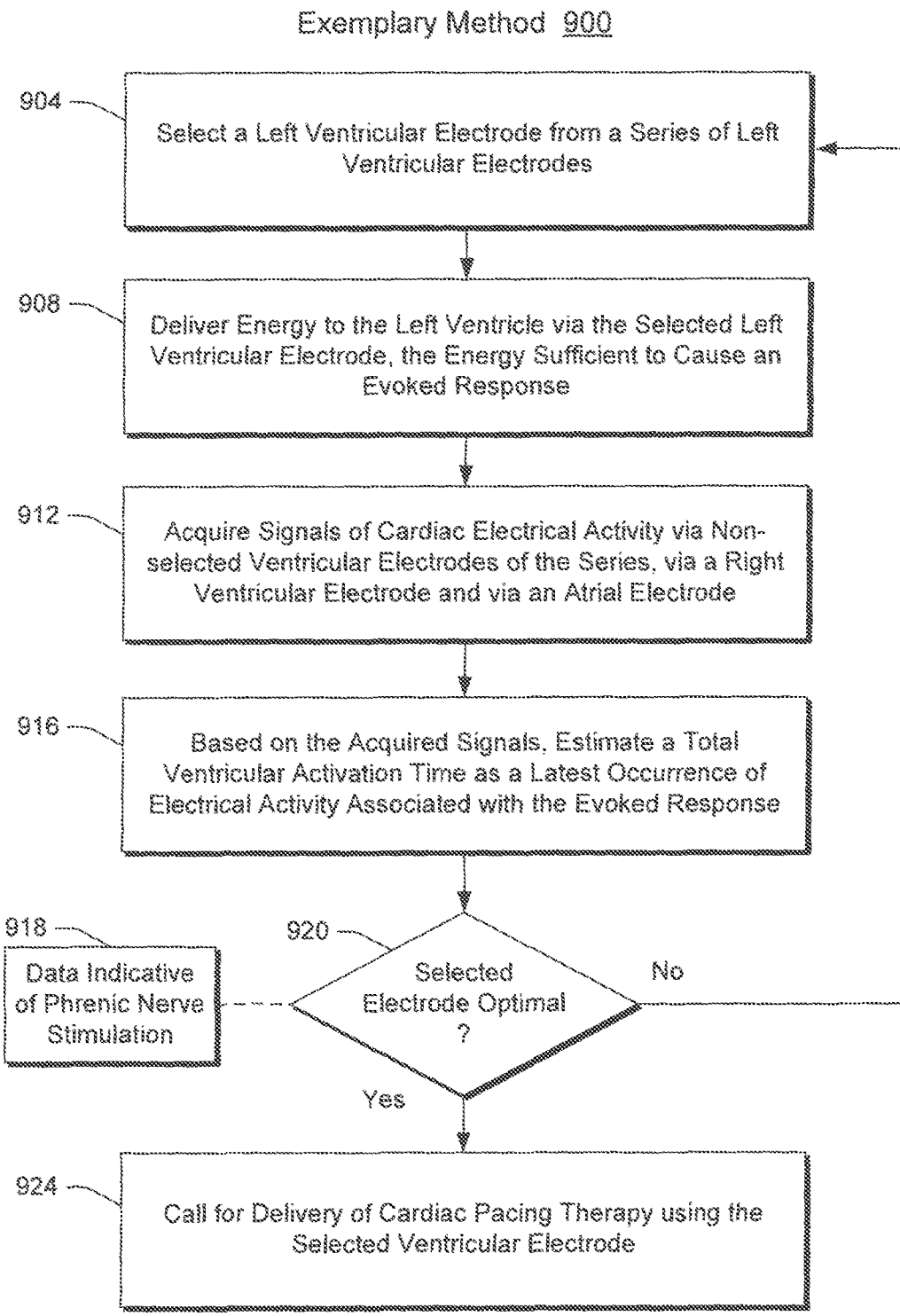
FIG. 9 is a block diagram of an exemplary method for optimizing a cardiac pacing therapy based at least in part on one or more ventricular activation times.

FIG. 9 shows an exemplary method 900 for optimizing cardiac pacing. The method 900 in particular pertains to delivery of energy using a left ventricular site and estimating a total ventricular activation time. As explained above, such a method may be suitably adapted to estimate a left ventricular activation time, a right ventricular activation time or left and right ventricular activation times. Further, while the method 900 is shown for delivery of energy using a left ventricular site, it may be suitably adapted for delivery of energy using a right ventricular site and for estimation of one or more of a total ventricular activation time, a right ventricular activation and a left ventricular activation time.

The method 900 commences in a selection block 904 that includes selecting a left ventricular electrode from a series of three or more left ventricular electrodes. A delivery block 908 provides for delivering energy to the left ventricle via the selected left ventricular electrode, the energy sufficient to cause an evoked response. An acquisition block 912 provides for acquiring signals of cardiac electrical activity associated with the evoked response via non-selected left ventricular electrodes of the series, via a right ventricular electrode and via an atrial electrode. An estimation block 916 provides for, based on the acquired signals, estimating a total ventricular activation time as a latest occurrence of cardiac electrical activity associated with the evoked response. A decision block 920 follows that provides for, based on the estimated total ventricular activation time, deciding if the selected left ventricular electrode is an optimal electrode for delivery of a cardiac pacing therapy. As shown in FIG. 9, an input block 918 may input additional information such as whether phrenic nerve stimulation occurred, which would possibly preclude the selected electrode from being an optimal electrode. If the decision block 920 decides that the selected left ventricular electrode is an optimal electrode for delivery of the cardiac pacing therapy, the method 900 enters a call block 924 that includes calling for delivery of the cardiac pacing therapy using the selected left ventricular electrode.

As described herein, the method 900 optionally includes one or more blocks to perform the following: delivering energy to the right ventricle via a right ventricular electrode, the energy sufficient to cause an evoked response; acquiring signals of cardiac electrical activity associated with the evoked response via the selected left ventricular electrode; and estimating the total activation time in a manner that considers an activation time based on the acquired signals via the selected left ventricular electrode as associated with the evoked response due to delivery of energy to the right ventricle.

The method 900 of FIG. 9 may include estimating a left ventricular activation time based on the acquired signals for the non-selected left ventricular electrodes or based on the acquired signals for the non-selected left ventricular electrodes and the atrial electrode. In such a method, the atrial electrode may be a left atrial electrode or a right atrial electrode. Various examples may include acquiring signals using a right atrial electrode and acquiring signals using a left atrial electrode.

With respect to a right ventricular activation time, the method 900 may include estimating such a time based on the acquired signals for the selected left ventricular electrode and acquired signals for a right atrial electrode.

Where the method 900 includes acquiring signals using an atrial electrode, it may include determining if a delay between the delivery of the energy and occurrence of cardiac electrical activity associated with the evoked response at the right ventricular electrode exceeds a delay between the delivery of the energy and occurrence of cardiac electrical activity associated with the evoked response at the atrial electrode and, if so, deciding that the selected left ventricular electrode is not an optimal electrode for delivery of the cardiac pacing therapy. Further, it may be determined or concluded that a conduction path from the selected left ventricular electrode to the right ventricular electrode includes conduction abnormalities.

As described herein, the exemplary method 900 may be adapted to include an acquisition block for acquiring signals of cardiac electrical activity associated with the evoked response via one or more skin-surface electrodes. In such a method, the estimating the total activation time can include considering an activation time based on the acquired signals via the one or more skin-surface electrodes. Further, such a method can include determining if a delay between the delivery of the energy and occurrence of cardiac electrical activity associated with the evoked response at the right ventricular electrode exceeds a delay between the delivery of the energy and occurrence of cardiac electrical activity associated with the evoked response at the one or more skin-surface electrodes and, if so, deciding that the selected left ventricular electrode is not an optimal electrode for delivery of the cardiac pacing therapy.

The method 900 of FIG. 9 may further include an analysis block for analyzing the signals of cardiac electrical activity acquired via the non-selected ventricular electrodes for indicia of functional conduction block. As mentioned, such signals of cardiac electrical activity may be unipolar signals (e.g., acquired using unipolar sensing configurations). As described below, indicia such as split potentials can be evidence of functional conduction block.

An exemplary implantable configured to implement the method 900 includes one or more connectors for electrically connecting a series of three or more left ventricular electrodes, at least one right ventricular electrode and at least one atrial electrode; control logic for selecting a left ventricular electrode from the series; control logic for delivering energy to the left ventricle via the selected left ventricular electrode, the energy sufficient to cause an evoked response; control logic for acquiring signals of cardiac electrical activity associated with the evoked response via non-selected left ventricular electrodes of the series, via at least one of the at least one right ventricular electrode and via at least one of the at least one atrial electrode; control logic for, based on the acquired signals, estimating a total ventricular activation time as a latest occurrence of cardiac electrical activity associated with the evoked response; control logic for, based on the estimated total ventricular activation time, deciding if the selected left ventricular electrode is an optimal electrode for delivery of a cardiac pacing therapy; and control logic for, if the selected left ventricular electrode is an optimal electrode for delivery of the cardiac pacing therapy, calling for delivery of the cardiac pacing therapy using the selected left ventricular electrode.

As mentioned, the method 900 may be suitably adapted for selection of a right ventricular electrode and acquisition of data sufficient to estimate one or more of a total ventricular activation time, a right ventricular activation time and a left ventricular activation time.

Figure 10:
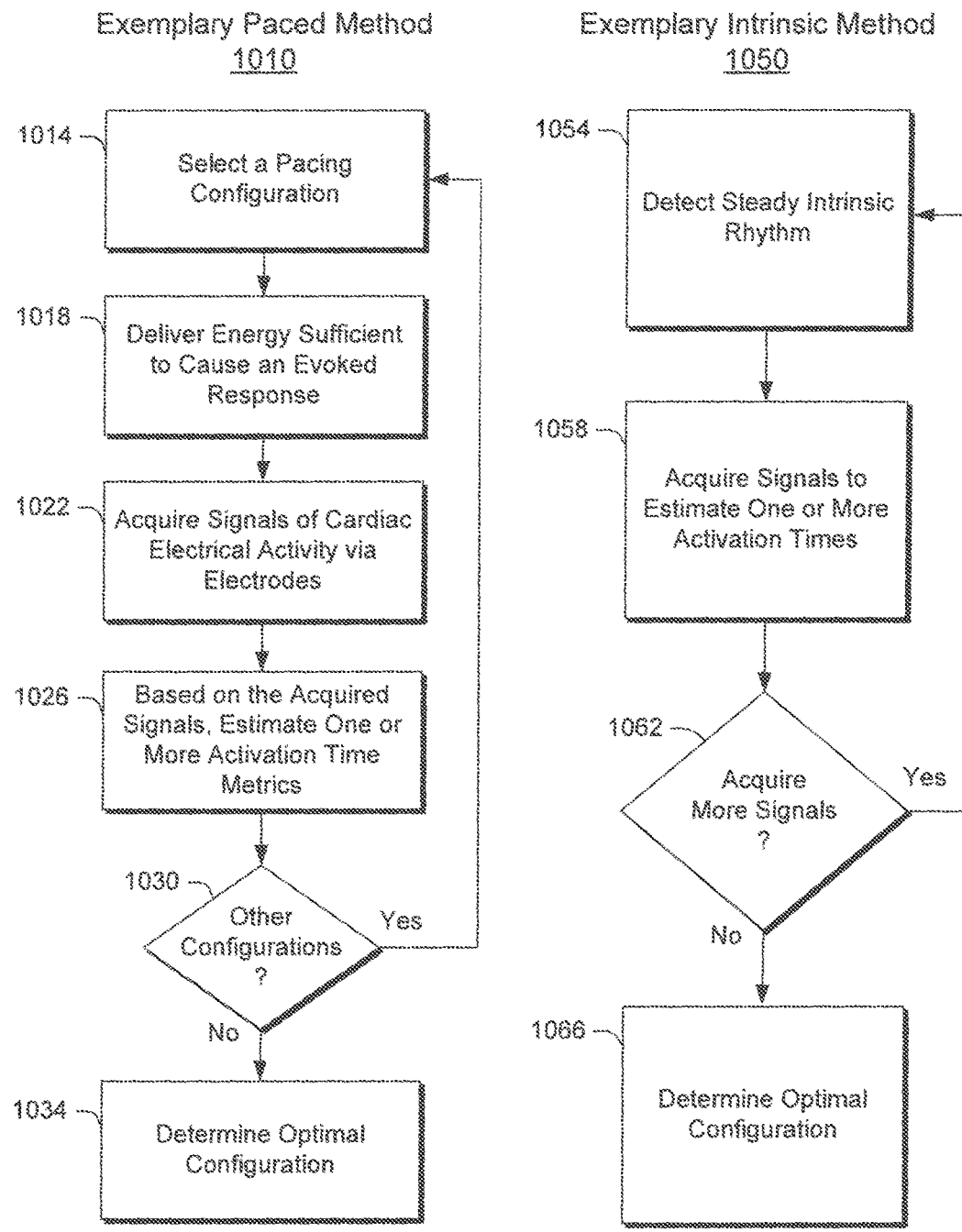
FIG. 10 is a block diagram of an exemplary method for optimizing a cardiac pacing therapy based on delivery of energy to the heart and an exemplary method for optimizing a cardiac pacing therapy based on intrinsic activation of the heart.

FIG. 10 shows an exemplary paced method 1010 and an exemplary intrinsic method 1050 for optimizing a cardiac therapy. The paced method 1010 includes a selection block 1014 for selecting a pacing configuration, a delivery block 1018 for delivering energy sufficient to cause an evoked response using the selected pacing configuration, an acquisition block 1022 for acquiring signals of cardiac electrical activity via electrodes, an estimation block 1026 for estimating one or more activation times based on the acquired signals, a decision block 1030 for deciding whether to select one or more other configurations and a determination block 1034 to determine an optimal configuration for delivery of a cardiac therapy.

The intrinsic method 1050 includes a detection block 1054 for detecting a steady intrinsic rhythm, an acquisition block 1058 for acquiring signals to estimate one or more activation times, a decision block 1062 to decide whether to acquire more signals and a determination block 1066 to determine an optimal configuration for pacing the heart, if so required, based on the one or more activation times.

As described herein, an exemplary method includes acquiring signals of cardiac electrical activity associated with an intrinsic activation of the heart via individual left ventricular electrodes of a series of three or more electrodes, via a right ventricular electrode and via an atrial electrode; and, based on the acquired signals, estimating a total ventricular activation time as a latest occurrence of cardiac electrical activity associated with the intrinsic activation of the heart. Such a method may also include estimating one or more of a right ventricular activation time and a left ventricular activation time. As mentioned, various techniques can include analyzing acquired data for indicia of functional conduction block. Aspects of functional conduction block are described in Auricchio et al., "Characterization of Left Ventricular Activation in Patients With Heart Failure and Left Bundle-Branch Block," Circulation 2004; 109:1133-1139, which is incorporated herein by reference. An exemplary method can include selecting a pacing site based in part on evidence of functional conduction block. For example, where an IEGM exhibits evidence of a line of functional block, an optimization process may avoid selecting an electrode within a certain distance from the line. By using a pacing electrode that is located a distance from a line of block, quicker LV activation and greater dP/dt may be achieved. In other words, where a line of functional block exists for the LV, as a pacing site is moved away from the line, LV activation and dP/dt tend to increase.

Figure 11:
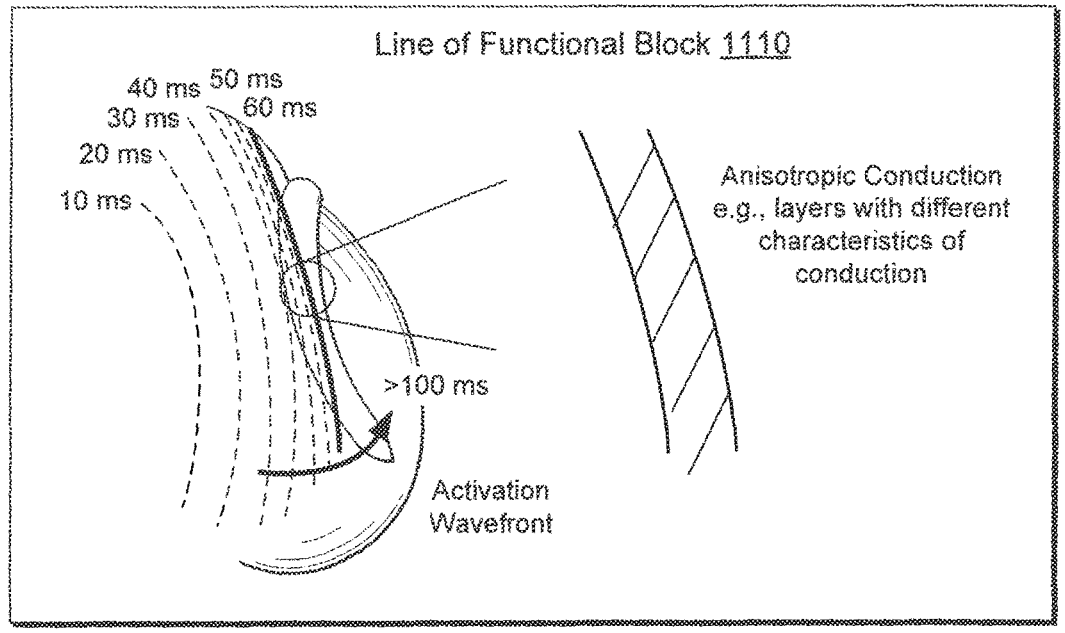
FIG. 11 is a diagram of various isochrones illustrating activation of myocardial tissue with respect to a "line" of functional block and a diagram of unipolar IEGMs for a series of electrodes positioned proximate to the functional block where at least one of the IEGMs includes indicia of functional block.
Figure 11:
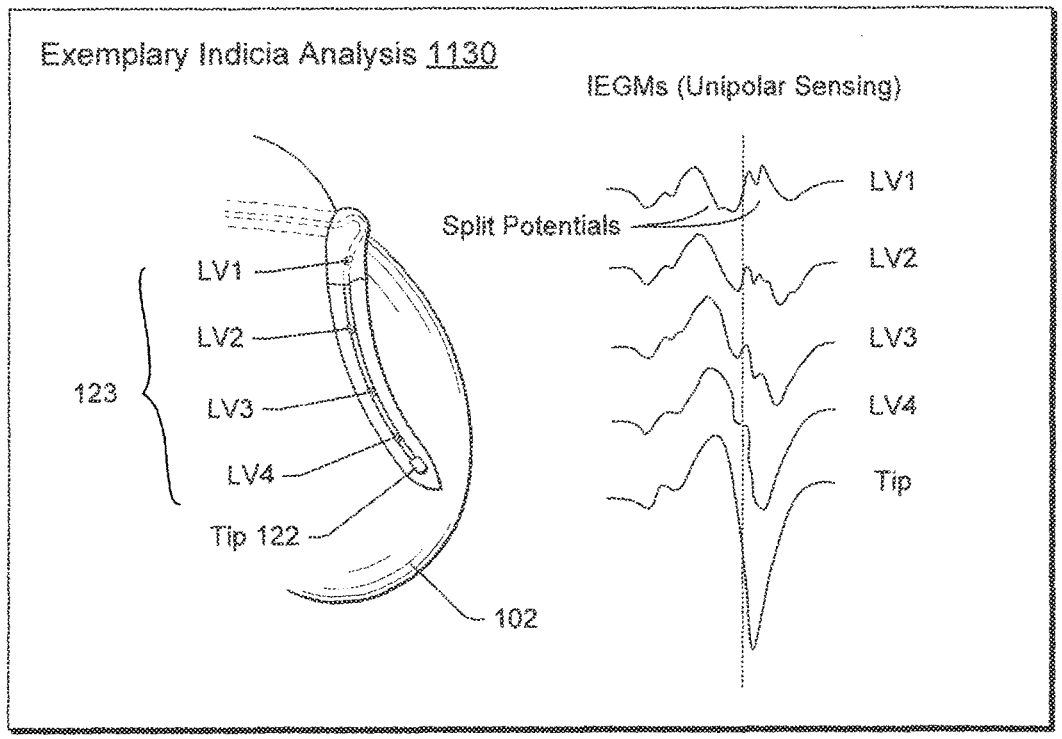

FIG. 11 shows an isochronal plot 1110 and a series of unipolar IEGMs 1130 that correspond to a line of functional block. The isochronal plot 1110 indicates how the activation times progressively increase approaching the line of functional block and where an activation wavefront passes below the line of functional block to activate tissue on the other side of the line. The IEGMs 1130 are shown along with the series of left ventricular electrodes 123 and a tip electrode 122. Various IEGMs exhibit so-called split potentials as indicia of functional block (e.g., evidence of functional block).

Figure 12:
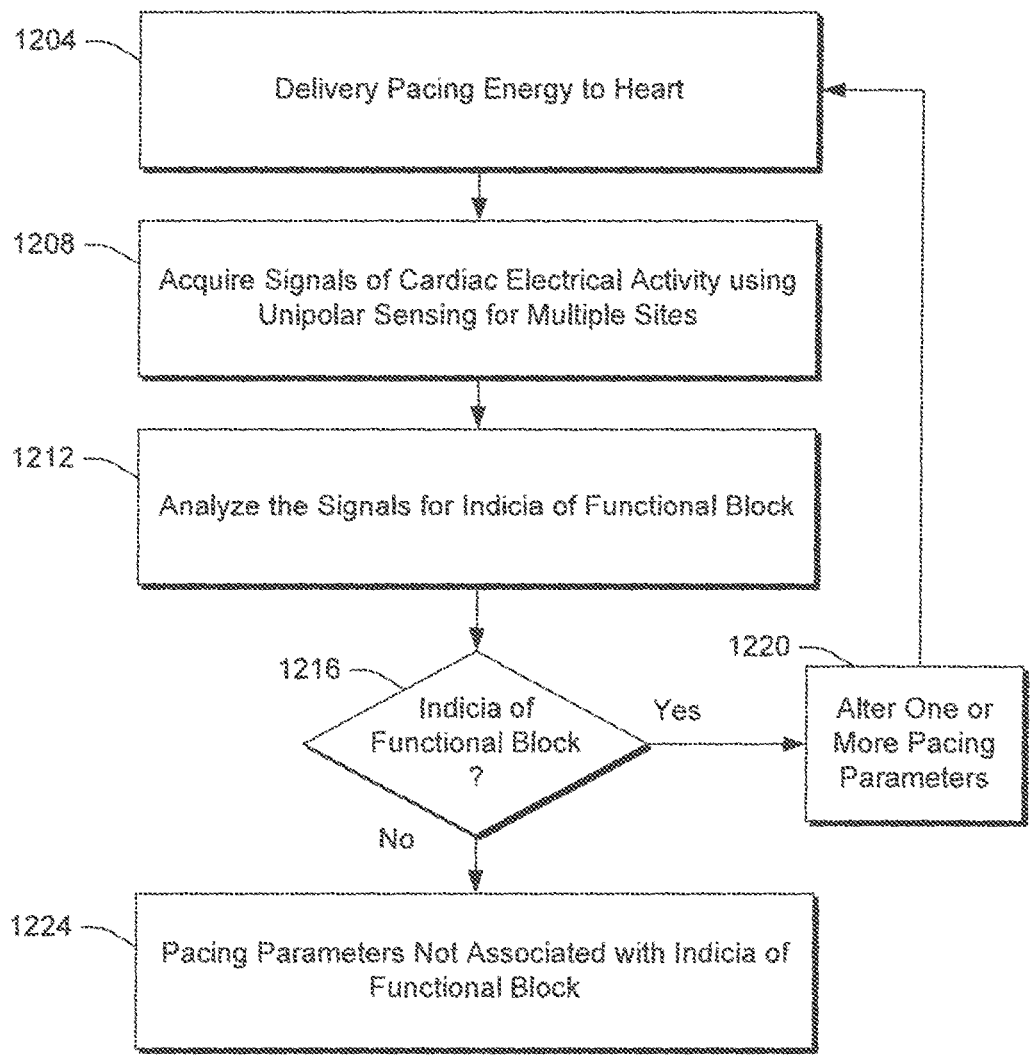
FIG. 12 is a block diagram of an exemplary method for deciding whether pacing parameters cause functional block.

FIG. 12 shows an exemplary method 1200 for determining whether a particular pacing configuration (e.g., selected electrode configuration, selected set of pacing parameters, etc.) exhibits indicia of functional block. The method 1200 commences in a delivery block 1204 that delivers energy to the heart according to a selected configuration. An acquisition block 1208 follows that acquires signals of cardiac electrical activity using unipolar sensing for multiple sites. An analysis block 1212 analyzes the signals for indicia of functional block, for example, indicia such as the split potentials shown in various IEGMs of FIG. 11. A decision block 1216 follows that decides if the signals include indicia representative of functional block. In the instance the decision block 1216 decides that no indicia exist, the method 1200 progresses to block 1224 that concludes that the pacing configuration is not associated with indicia of functional block. However, if the decision block 1216 decides that indicia do exist, then the method 1200 continues to block 1220 to alter one or more parameters of the configuration and to repeat the delivering per the delivery block 1204, etc.

As described herein, the method 1200 may be integrated with various other exemplary methods to optimize pacing. Specifically, various exemplary methods can include an analysis block such as the block 1212 that analyzes IEGMs for indicia of functional block. In general, functional block should be avoided for optimal pacing.

Exemplary External Programmer

Figure 13:
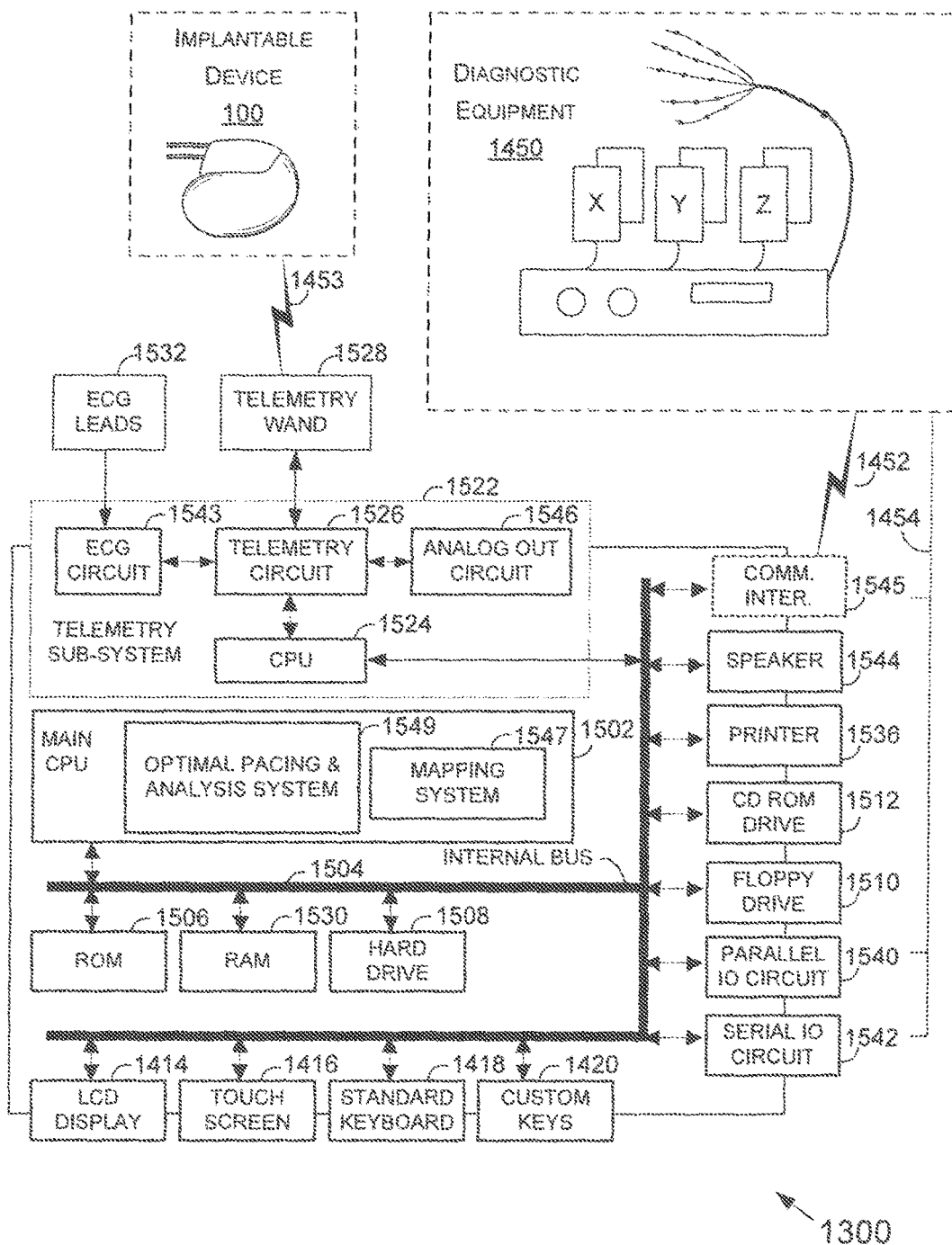
FIG. 13 is an exemplary system for acquiring information and analyzing such information.

FIG. 13 illustrates pertinent components of an external programmer 1300 for use in programming an implantable medical device 100 (see, e.g., FIGS. 1 and 2). The external programmer 1300 optionally receives information from other diagnostic equipment 1350, which may be a computing device capable of acquiring motion information related to cardiac mechanics. For example, the equipment 1350 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 1300 in distinguishing respiratory motion from cardiac.

Briefly, the programmer 1300 permits a clinician or other user to program the operation of the implanted device 100 and to retrieve and display information received from the implanted device 100 such as IEGM data and device diagnostic data. Where the device 100 includes a module such as the conduction delay module 239, then the programmer 1300 may instruct the device 100 to measure conduction delays and to communicate measured conduction delays to the programmer via a communication link 1453. The programmer 1300 may also instruct a device or diagnostic equipment to deliver current to generate one or more potential fields within a patient's body where the implantable device 100 may be capable of measuring potentials associated with the field(s).

The external programmer 1300 may be configured to receive and display ECG data from separate external ECG leads 1532 that may be attached to the patient. The programmer 1300 optionally receives ECG information from an ECG unit external to the programmer 1300. The programmer 1300 may use techniques to account for respiration.

Depending upon the specific programming, the external programmer 1300 may also be capable of processing and analyzing data received from the implanted device 100 and from ECG leads 1532 to, for example, render diagnosis as to medical conditions of the patient or to the operations of the implanted device 100. As noted, the programmer 1300 is also configured to receive data representative of conduction time delays from the atria to the ventricles and to determine, therefrom, an optimal or preferred configuration for pacing. Further, the programmer 1300 may receive information such as ECG information, IEGM information, information from diagnostic equipment, etc., and determine one or more metrics for optimizing therapy.

Considering the components of programmer 1300, operations of the programmer are controlled by a CPU 1502, which may be a generally programmable microprocessor or microcontroller or may be a dedicated processing device such as an application specific integrated circuit (ASIC) or the like. Software instructions to be performed by the CPU are accessed via an internal bus 1504 from a read only memory (ROM) 1506 and random access memory 1530. Additional software may be accessed from a hard drive 1508, floppy drive 1510, and CD ROM drive 1512, or other suitable permanent or removable mass storage device. Depending upon the specific implementation, a basic input output system (BIOS) is retrieved from the ROM 1506 by CPU 1502 at power up. Based upon instructions provided in the BIOS, the CPU 1502 "boots up" the overall system in accordance with well-established computer processing techniques.

Once operating, the CPU 1502 displays a menu of programming options to the user via an LCD display 1414 or other suitable computer display device. To this end, the CPU 1502 may, for example, display a menu of specific programming parameters of the implanted device 100 to be programmed or may display a menu of types of diagnostic data to be retrieved and displayed. In response thereto, the clinician enters various commands via either a touch screen 1416 overlaid on the LCD display or through a standard keyboard 1418 supplemented by additional custom keys 1420, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to mapping of metrics (e.g., for patterns of conduction), the CPU 1502 includes a 3-D mapping system 1547 and an associated data analysis system 1549. The systems 1547 and 1549 may receive position information and physiological information from the implantable device 100 and/or diagnostic equipment 1450. The data analysis system 1549 optionally includes control logic to associate information and to make one or more conclusions based on metrics, for example, as indicated in FIG. 3 to optimize delivery of therapy (e.g., to optimize a pacing configuration).

Where information is received from the implanted device 100, a telemetry wand 1528 may be used. Other forms of wireless communication exist as well as forms of communication where the body is used as a "wire" to communicate information from the implanted device 100 to the programmer 1300.

If information is received directly from diagnostic equipment 1450, any appropriate input may be used, such as parallel IO circuit 1540 or serial IO circuit 1542. Motion information received via the device 100 or via other diagnostic equipment 1450 may be analyzed using the mapping system 1547. In particular, the mapping system 1547 (e.g., control logic) may identify positions within the body of a patient and associate such positions with one or more electrodes where such electrodes may be capable of delivering stimulation energy to the heart, performing other actions or be associated with one or more sensors.

A communication interface 1545 optionally allows for wired or wireless communication with diagnostic equipment 1450 or other equipment (e.g., equipment to ablate or otherwise treat a patient). The communication interface 1545 may be a network interface connected to a network (e.g., intranet, Internet, etc.).

A map or model of cardiac information may be displayed using display 1414 based, in part, on 3-D heart information and optionally 3-D torso information that facilitates interpretation of information. Such 3-D information may be input via ports 1540, 1542, 1545 from, for example, a database, a 3-D imaging system, a 3-D location digitizing apparatus (e.g., stereotactic localization system with sensors and/or probes) capable of digitizing the 3-D location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 1300 optionally records procedures and allows for playback (e.g., for subsequent review). For example, a heart map and all of the electrical activation data, mechanical activation data, etc., may be recorded for subsequent review, perhaps if an electrode needs to be repositioned or one or more other factors need to be changed (e.g., to achieve an optimal configuration). Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 1522 may include its own separate CPU 1524 for coordinating the operations of the telemetry subsystem. In a dual CPU system, the main CPU 1502 of programmer communicates with telemetry subsystem CPU 1524 via internal bus 1504. Telemetry subsystem additionally includes a telemetry circuit 1526 connected to telemetry wand 1528, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 1300 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 1300 (e.g., within a random access memory (RAM) 1530, hard drive 1508, within a floppy diskette placed within floppy drive 1510). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 1300 has a communication link to an external storage device or network storage device, then information may be stored in such a manner (e.g., on-site database, off-site database, etc.). The programmer 1300 optionally receives data from such storage devices.

A typical procedure may include transferring all patient and device diagnostic data stored in an implanted device 100 to the programmer 1300. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 1522 receives ECG signals from ECG leads 1532 via an ECG processing circuit 1534. As with data retrieved from the implanted device 100, signals received from the ECG leads are stored within one or more of the storage devices of the programmer 1300. Typically. ECG leads output analog electrical signals representative of the ECG. Accordingly, ECG circuit 1534 includes analog to digital conversion circuitry for converting the signals to digital data appropriate for further processing within programmer 1300. Depending upon the implementation, the ECG circuit 1543 may be configured to convert the analog signals into event record data for ease of processing along with the event record data retrieved from the implanted device. Typically, signals received from the ECG leads 1532 are received and processed in real time.

Thus, the programmer 1300 is configured to receive data from a variety of sources such as, but not limited to, the implanted device 100, the diagnostic equipment 1450 and directly or indirectly via external ECG leads (e.g., subsystem 1522 or external ECG system). The diagnostic equipment 1450 includes wired 1454 and/or wireless capabilities 1452 which optionally operate via a network that includes the programmer 1300 and the diagnostic equipment 1450 or data storage associated with the diagnostic equipment 1450.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 1502, the programming commands are converted to specific programming parameters for transmission to the implanted device 100 via telemetry wand 1528 to thereby reprogram the implanted device 100 or other devices, as appropriate.

Prior to reprogramming specific parameters, the clinician may control the external programmer 1300 to display any or all of the data retrieved from the implanted device 100, from the ECG leads 1532, including displays of ECGs, IEGMs, statistical patient information (e.g., via a database or other source), diagnostic equipment 1450, etc. Any or all of the information displayed by programmer may also be printed using a printer 1536.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, VV delay may be adjusted to achieve still further enhancements in cardiac function.

Programmer 1300 optionally includes a modem to permit direct transmission of data to other programmers via the public switched telephone network (PSTN) or other interconnection line, such as a T1 line or fiber optic cable. Depending upon the implementation, the modem may be connected directly to internal bus 1504 may be connected to the internal bus via either a parallel port 1540 or a serial port 1542.

Other peripheral devices may be connected to the external programmer via the parallel port 1540, the serial port 1542, the communication interface 1545, etc. Although one of each is shown, a plurality of input output (IO) ports might be provided. A speaker 1544 is included for providing audible tones to the user, such as a warning beep in the event improper input is provided by the clinician. Telemetry subsystem 1522 additionally includes an analog output circuit 1546 for controlling the transmission of analog output signals, such as IEGM signals output to an ECG machine or chart recorder.

With the programmer 1300 configured as shown, a clinician or other user operating the external programmer is capable of retrieving, processing and displaying a wide range of information received from the ECG leads 1532, from the implanted device 100, the diagnostic equipment 1450, etc., and to reprogram the implanted device 100 or other implanted devices if needed. The descriptions provided herein with respect to FIG. 13 are intended merely to provide an overview of the operation of programmer and are not intended to describe in detail every feature of the hardware and software of the device and is not intended to provide an exhaustive list of the functions performed by the device 1300. Other devices, particularly computing devices, may be used.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the

What is claimed is:
1. A method comprising:
selecting a left ventricular electrode from a series of three or more left ventricular electrodes;
delivering energy to the left ventricle via the selected left ventricular electrode, the energy sufficient to cause an evoked response;
acquiring signals of cardiac electrical activity associated with the evoked response via non-selected left ventricular electrodes of the series, via a right ventricular electrode and via an atrial electrode;

measuring a delay between the evoked response and the cardiac electrical activity associated with the evoked response acquired by the non-selected left ventricular electrodes, the right ventricular electrode and the atrial electrode;

based on the acquired signals, estimating a total ventricular activation time as a function of the longest measured delay between the evoked response and the cardiac electrical activity associated with the evoked response acquired by the non-selected left ventricular electrodes, the right ventricular electrode and the atrial electrode;

based on the estimated total ventricular activation time, deciding if the selected left ventricular electrode comprises an optimal electrode for delivery of a cardiac pacing therapy; and if the selected left ventricular electrode comprises an optimal electrode for delivery of the cardiac pacing therapy, calling for delivery of the cardiac pacing therapy using the selected left ventricular electrode.

2. The method of claim 1 further comprising:

delivering energy to the right ventricle via a right ventricular electrode, the energy sufficient to cause an evoked response;

acquiring signals of cardiac electrical activity associated with the evoked response via the selected left ventricular electrode; and wherein the estimating the total activation time comprises considering an activation time based on the acquired signals via the selected left ventricular electrode as associated with the evoked response due to delivery of energy to the right ventricle.

3. The method of claim 1 further comprising, based on the acquired signals for the non-selected left ventricular electrodes, estimating a left ventricular activation time.

4. The method of claim 1 further comprising, based on the acquired signals for the non-selected left ventricular electrodes and the atrial electrode, estimating a left ventricular activation time.

5. The method of claim 1 further comprising, based on the acquired signals for the non-selected left ventricular electrode and the atrial electrode, estimating a right ventricular activation time.

6. The method of claim 1 further comprising determining if a delay between the delivery of the energy and occurrence of cardiac electrical activity associated with the evoked response at the right ventricular electrode exceeds a delay between the delivery of the energy and occurrence of cardiac electrical activity associated with the evoked response at the atrial electrode and, if so, deciding that the selected left ventricular electrode does not comprise an optimal electrode for delivery of the cardiac pacing therapy.

7. A method comprising:

acquiring signals of cardiac electrical activity associated with an intrinsic activation of the heart via individual left ventricular electrodes of a series of three or more electrodes, via a right ventricular electrode and via an atrial electrode;

measuring a delay between the intrinsic activation and the cardiac electrical activity associated with the intrinsic activation acquired by the individual left ventricular electrodes, the right ventricular electrode and the atrial electrode; and based on the acquired signals, estimating a total ventricular activation time as a function of the longest measured delay between the evoked response and the cardiac electrical activity associated with the intrinsic activation of the heart acquired by the left ventricular electrodes, the right ventricular electrode and the atrial electrode.

* * * * *